United States Patent
Nomoto

(10) Patent No.: US 10,161,857 B2
(45) Date of Patent: Dec. 25, 2018

(54) METAMATERIAL OPTICAL MEMBER, LIGHT DETECTION DEVICE, LASER EXCITATION LIGHT SOURCE, AND MEASURING DEVICE

(71) Applicant: HAMAMATSU PHOTONICS K.K., Hamamatsu-shi, Shizuoka (JP)

(72) Inventor: Yoshiro Nomoto, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/301,764

(22) PCT Filed: Apr. 3, 2015

(86) PCT No.: PCT/JP2015/060651
§ 371 (c)(1),
(2) Date: Oct. 4, 2016

(87) PCT Pub. No.: WO2015/156231
PCT Pub. Date: Oct. 15, 2015

(65) Prior Publication Data
US 2017/0023466 A1    Jan. 26, 2017

(30) Foreign Application Priority Data
Apr. 7, 2014  (JP) ................. 2014-078820

(51) Int. Cl.
*G01N 21/00* (2006.01)
*G01N 21/25* (2006.01)
(Continued)

(52) U.S. Cl.
CPC ....... *G01N 21/255* (2013.01); *G01N 21/0303* (2013.01); *G01N 21/05* (2013.01);
(Continued)

(58) Field of Classification Search
CPC . G02B 1/11; G02B 6/02; G02B 1/002; G01N 21/6428; G01N 21/27; G01N 21/255; G01N 21/0303; G01N 21/05; G01N 2201/06113; G01N 21/59; G01N 21/85; G01N 21/645

USPC ................................. 356/328, 436, 498
See application file for complete search history.

(56) References Cited

U.S. PATENT DOCUMENTS

| | | | |
|---|---|---|---|
| 4,541,439 A * | 9/1985 | Hon ................. | A61B 5/035 600/504 |
| 2004/0011975 A1* | 1/2004 | Nicoli ............. | G01N 15/0227 250/574 |

(Continued)

FOREIGN PATENT DOCUMENTS

| | | |
|---|---|---|
| JP | H07-204158 A | 8/1995 |
| JP | H08-234254 A | 9/1996 |

(Continued)

OTHER PUBLICATIONS

International Preliminary Report on Patentability dated Oct. 20, 2016 for PCT/JP2015/060651.

(Continued)

*Primary Examiner* — Isiaka Akanbi
(74) *Attorney, Agent, or Firm* — Drinker Biddle & Reath LLP

(57) ABSTRACT

A metamaterial optical member 100 includes a light collecting optical member 1 having a light-entering surface IN1 and a light-exiting surface OUT1 and having a light collecting function and an antireflection film 2 disposed in the light-exiting surface OUT1 of the light collecting optical member 1. The antireflection film 2 has a first metamaterial structure in which a refractive index is gradually reduced in the light travelling direction. The metamaterial optical member 100 includes the antireflection film 2 having the metamaterial structure, thereby externally extracting light.

9 Claims, 47 Drawing Sheets

(51) Int. Cl.
| | |
|---|---|
| G02B 1/00 | (2006.01) |
| G02B 1/115 | (2015.01) |
| G01N 21/27 | (2006.01) |
| G01N 21/64 | (2006.01) |
| G02B 1/11 | (2015.01) |
| G02B 6/02 | (2006.01) |
| G01N 21/03 | (2006.01) |
| G01N 21/05 | (2006.01) |
| G01N 21/85 | (2006.01) |
| G01N 21/59 | (2006.01) |

(52) U.S. Cl.
CPC ......... *G01N 21/27* (2013.01); *G01N 21/6428* (2013.01); *G02B 1/002* (2013.01); *G02B 1/11* (2013.01); *G02B 1/115* (2013.01); *G02B 6/02* (2013.01); *G01N 21/59* (2013.01); *G01N 21/645* (2013.01); *G01N 21/85* (2013.01); *G01N 2201/06113* (2013.01)

(56) References Cited

U.S. PATENT DOCUMENTS

| | | | |
|---|---|---|---|
| 2010/0110559 A1 | 5/2010 | Cai et al. | |
| 2011/0160542 A1 | 6/2011 | Ahn | |
| 2012/0176668 A1* | 7/2012 | Saito | G02B 1/04 359/357 |
| 2015/0130973 A1* | 5/2015 | Saito | G02B 3/0087 348/252 |
| 2016/0370303 A1* | 12/2016 | Schmitz | G01N 23/083 |

FOREIGN PATENT DOCUMENTS

| | | |
|---|---|---|
| JP | 2005-533262 A | 11/2005 |
| JP | 2005-331784 A | 12/2005 |
| JP | 2009-250825 A | 10/2009 |
| JP | 2011-158665 A | 8/2011 |
| JP | A-2013-506884 | 2/2013 |
| JP | 2013-050688 A | 3/2013 |
| JP | 2014-036152 A | 2/2014 |
| WO | WO-2004/010113 A1 | 1/2004 |
| WO | WO 2011/044239 A1 | 4/2011 |
| WO | WO-2013/171969 A1 | 11/2013 |

OTHER PUBLICATIONS

Yingran He et al., "Nanoscale metamaterial optical waveguides with ultrahigh refractive indices," Journal of the Optical Society of America, Aug. 29, 2012, pp. 2559-2566, vol. 29, No. 9.

\* cited by examiner

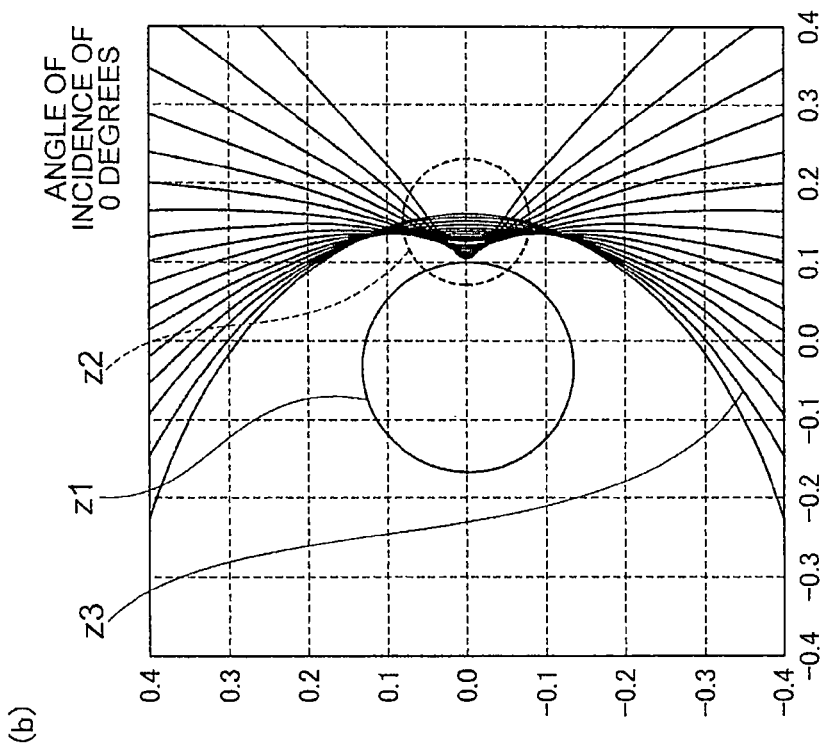
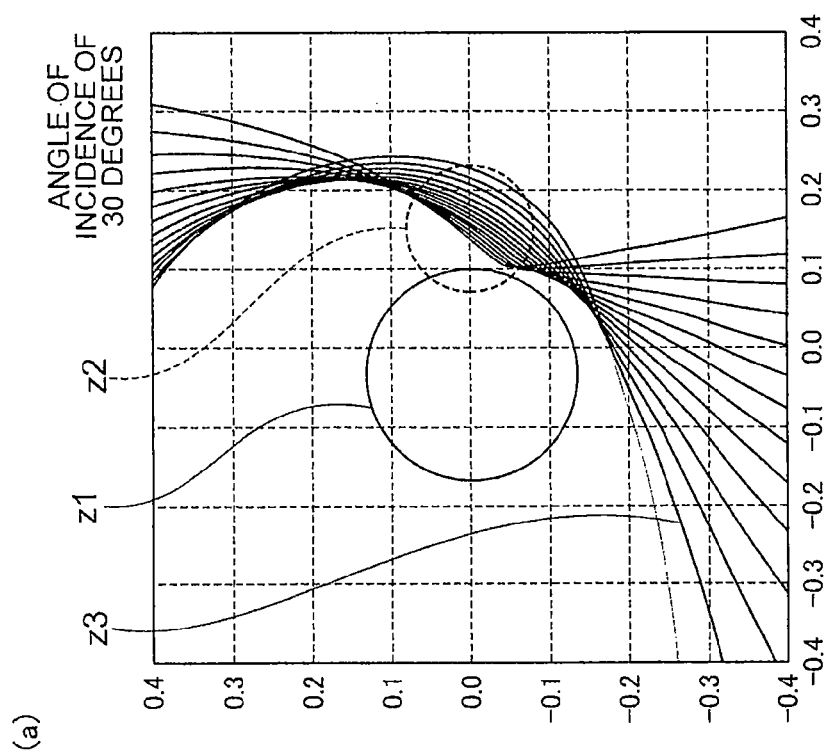
Fig. 47

METAMATERIAL OPTICAL MEMBER, LIGHT DETECTION DEVICE, LASER EXCITATION LIGHT SOURCE, AND MEASURING DEVICE

TECHNICAL FIELD

The present invention relates to a metamaterial optical member and a light detection device, a laser excitation light source, and a measuring device used in the metamaterial optical member.

BACKGROUND ART

A conventional metamaterial optical member is disclosed in, for example, Patent Literature 1. In Patent Literature 1, a refractive index distribution type lens including a first region having a low refractive index and a second region having a high refractive index is disclosed and a refractive index distribution structure of the lens is configured by laminating metamaterials.

When the metamaterials are used, it is possible to artificially manufacture an optical member having a refractive index absent in the natural world (the square root of (permittivity $\mu$×permeability $\varepsilon$): $(\varepsilon\mu)^{1/2}$). That is, the metamaterial has a small metal piece, for example, as shown in Non-Patent Literature 1. This metamaterial configures an optical waveguide in which a silver layer and a germanium layer are laminated and which extends in a direction perpendicular to a lamination direction, a thickness of the silver layer is 4 nm, and a thickness of the germanium layer is 6 nm. A refractive index of 35 or more is implemented using this nanoscale structure.

When desired permeability of the metamaterial is obtained by forming a structure in a size less than or equal to ⅙ of an incident wavelength responsive to a magnetic field component of light (electromagnetic waves) or desired permittivity is obtained by forming a structure responsive to an electric field component of light (electromagnetic waves) as in the above-described Non-Patent Literature, it is possible to individually design the permittivity and the permeability defining the refractive index. Thus, it is possible to implement a refractive index material absent in the natural world. Because light collection impossible in the general lens is also possible when the metamaterial is used, applications in various fields are expected.

CITATION LIST

Patent Literature

[Patent Literature 1] Japanese Unexamined Patent Publication No. 2013-506884

Non Patent Literature

[Non-Patent Literature 1] Yingran He, Sailing He, Jie Gao, Xiaodong Yang, "Nanoscale metamaterial optical waveguides with ultrahigh refractive indices," Journal of the Optical Society of America, B, Vol. 29, No. 9, pp. 2559-2566, Aug. 29, 2012

SUMMARY OF INVENTION

Technical Problem

However, when the metamaterial optical member of the high refractive index is used, it is significantly difficult to transmit and receive light to and from the outside. This is because light is reflected due to the mismatch of the refractive index value in an interface between a region within a member of a high refractive index and an external space (air) of a low refractive index and therefore it is impossible to extract light to an external space side.

The present invention has been made in view of the above-described problem and an objective of the invention is to provide a metamaterial optical member capable of transmitting and receiving light to and from an outside and a light detection device, a laser excitation light source, and a measuring device using the metamaterial optical member.

Solution to Problem

To solve the above-described problem, a first metamaterial optical member includes a light collecting optical member having a light-entering surface and a light-exiting surface and having a light collecting function; and an antireflection film disposed in the light-exiting surface of the light collecting optical member, wherein the antireflection film has a first metamaterial structure in which a refractive index is gradually reduced in the light travelling direction.

A refractive index of a region in which light is collected by the light collecting optical member is set to be higher than that of its peripheral region. Accordingly, the antireflection film of a first metamaterial structure is provided so that light collected in the light-exiting surface of the light collecting optical member is externally extracted without being reflected by the light-exiting surface. Because it is possible to form a refractive index change from a high refractive index absent in the natural world to a low refractive index using the metamaterial structure, it is possible to externally extract light which is not externally extracted conventionally.

Also, in a second metamaterial optical member, the light collecting optical member has a second metamaterial structure in which a refractive index gradually increases from the light-entering surface to the light-exiting surface.

In this case, because the light collecting optical member has the second metamaterial structure and can form the refractive index change absent in the natural world, light collection characteristics which cannot be implemented in optics using conventional geometries can be executed. It is possible to externally extract light collected in the light-exiting surface even when light collection of such a special state is performed because the antireflection film of the first metamaterial structure is provided.

In a third metamaterial optical member, the light-exiting surface includes a concave surface.

In this case, a light collection position by the light collecting optical member is set to be positioned inside the concave surface, so that the collected light can be used within an internal space of a concave portion.

In a fourth metamaterial optical member, the light-exiting surface includes a second concave surface continuous to a part of the concave surface and having a smaller opening size than the concave surface.

When the light collection position is positioned at a deeper position in the light collecting optical member than the concave surface, the second concave surface in which the light collection position is internally positioned is partially provided. The second concave surface can be formed even when a large portion of the light collecting optical member is not processed because the opening size is small.

In a fifth metamaterial optical member, the light-exiting surface includes a flat surface. In this case, there is an advantage in that it is unnecessary to perform a process of forming a concave surface in the light-exiting surface.

When the above-described metamaterial optical member is used, it is possible to configure various devices.

That is, a first light detection device includes the third or fourth metamaterial optical member having the above-described concave surface; and a light detector arranged inside a concave surface of the metamaterial optical member.

When light to be detected is incident on the light-entering surface of the light collecting optical member, the light to be detected is collected and incident on the light detector arranged inside the concave surface via the antireflection film. Therefore, the light detector can detect the light to be detected. A photomultiplier, a photodiode, a solid-state imaging element, or the like can be used as the light detector.

Also, a first laser excitation light source includes the third or fourth metamaterial optical member having the above-described concave surface; and a laser medium arranged inside a concave surface of the metamaterial optical member.

When excitation light of the laser medium is incident on the light-entering surface of the light collecting optical member, the light is collected and incident on the laser medium arranged inside the concave surface via the antireflection film. Therefore, the excitation light can excite the laser medium. It is possible to use an optical fiber or the like to which a rare earth element such as Er, Yb, or Nd is added as the laser medium.

Also, a first measuring device includes the third or fourth metamaterial optical member having the above-described concave surface; a medium flow path arranged inside a concave surface of the metamaterial optical member; and a light detector configured to detect light from the medium flow path.

Materials of various inspection targets can flow within a medium flow path. For example, in the case in which a labeling material for generating fluorescence when light of a specific wavelength is absorbed flows inside a medium flow path, the light detector can detect light generated from the material and the analysis of the material, etc. can be performed on the basis of the detected light. Also, when an opaque liquid flows as a medium, it is possible to inspect the transparency of the medium by detecting an intensity of light transmitted through the medium.

Also, a second laser detection device includes the fifth metamaterial optical member having the above-described flat surface; and a light detector arranged opposite to the flat surface of the metamaterial optical member.

When light to be detected is incident on the light-entering surface of the light collecting optical member, the light to be detected is collected and incident on the light detector via the antireflection film disposed in the flat surface. Therefore, the light detector can detect the light to be detected. A photomultiplier, a photodiode, a solid-state imaging element, or the like can be used as the light detector. In particular, when the flatness of the flat surface is used, there is an advantage in that solid-state imaging elements are easily arranged opposite to each other.

A second laser excitation light source includes the fifth metamaterial optical member having the above-described flat surface; and a laser medium arranged opposite to the flat surface of the metamaterial optical member.

When excitation light of the laser medium is incident on the light-entering surface of the light collecting optical member, the light is collected and incident on the laser medium arranged opposite to the antireflection film via the antireflection film disposed in the flat surface. Therefore, the excitation light can excite the laser medium. An element having a plate shape in which an opposite surface is flat as well as an optical fiber to which a rare earth element such as Er, Yb, or Nd is added can be used as the laser medium.

A second measuring device includes the fifth metamaterial optical member; a medium flow path arranged opposite to the flat surface of the metamaterial optical member; and a light detector configured to detect light from the medium flow path.

The materials of the inspection targets described above can flow within a medium flow path. The light detector can detect light generated from the material inside the medium flow path and the analysis of the material, etc. can be performed on the basis of the detected light. Also, when an opaque liquid flows as a medium, it is possible to inspect the transparency of the medium by detecting an intensity of light transmitted through the medium.

Also, when light emission from the laser medium, a medium flow path, or the like is detected, a (second) metamaterial optical member to be used in combination with the above-described (first) metamaterial optical member can be used. The (second) metamaterial optical member of a side at which light is received as described above includes a light transfer member having a light-entering surface and a light-exiting surface; and an antireflection film disposed in the light-entering surface of the light transfer member, wherein the light transfer member has a metamaterial structure in which a refractive index is gradually reduced from the light-entering surface to the light-exiting surface. Also, the (second) metamaterial optical member and the (first) metamaterial optical member may have the same structure.

Because a region of the light-entering surface side of the (second) metamaterial optical member has a high refractive index, it is difficult to cause light to be incident from the outside. Thus, when light is caused to be incident from the outside to the light-entering surface of the light transfer member, the antireflection film functions and the transfer loss of light is suppressed. Because the metamaterial structure can form the refractive index absent in the natural world, the (second) metamaterial optical member can transfer light symmetric to the (first) metamaterial optical member and therefore a design is simplified by performing a common design of a refractive index distribution or the like.

As described above, in the case of a metamaterial optical member of a light-receiving type, the light-entering surface includes a concave surface and receives light from a medium flow path or a laser medium arranged within the concave surface. The light transfer member transfers the incident light to output the transferred light from the light-exiting surface.

Advantageous Effects of Invention

According to a metamaterial optical member of the present invention, it is possible to transmit and receive light to and from the outside. The metamaterial optical member can be applied to a light detection device, a laser excitation light source, and a measuring device.

BRIEF DESCRIPTION OF DRAWINGS

FIG. 47 is a diagram for describing a beam group in the vicinity of an invisibility cloak.

DESCRIPTION OF EMBODIMENTS

Figure 1:
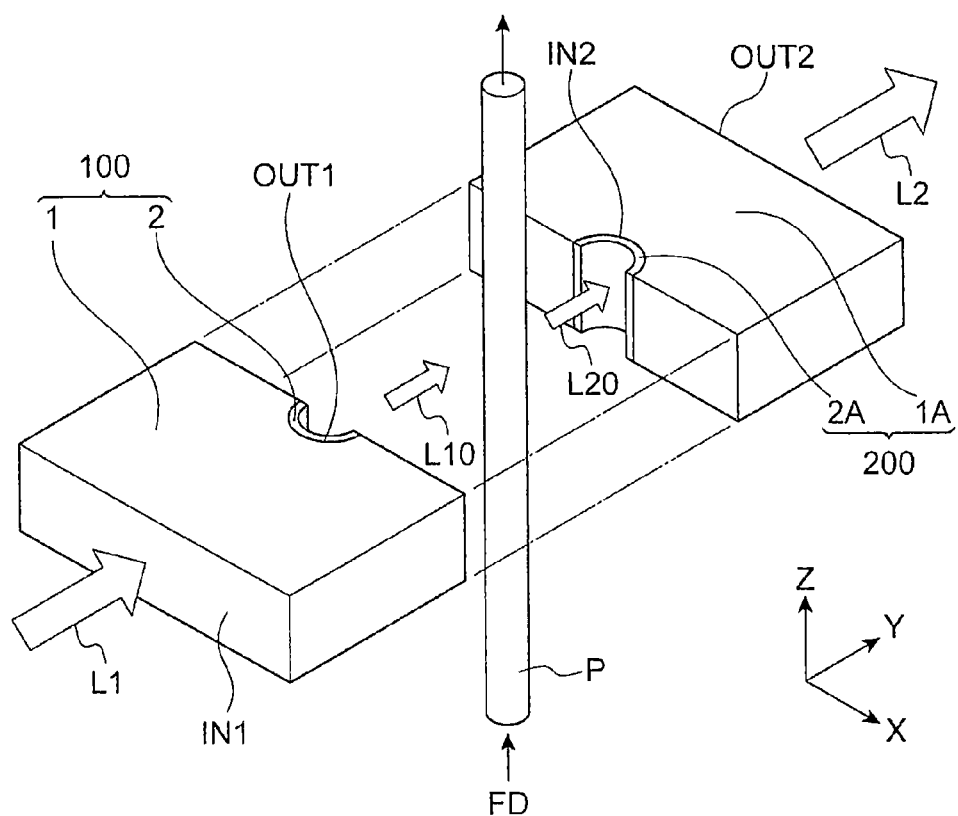
FIG. 1 is a perspective view illustrating an exploded detection unit of a measuring device.

Hereinafter, a metamaterial optical member and a light detection device, a laser excitation light source, and a measuring device using the metamaterial optical member according to embodiments will be described. Also, the same or like elements in the drawings are assigned the same reference signs and redundant description thereof will be omitted.

First, a measuring device including a pair of metamaterial optical members will be described.

FIG. 1 is a perspective view illustrating an exploded detection unit of the measuring device. Also, in the following description, an XYZ three-dimensional orthogonal coordinate system is set.

A first metamaterial optical member 100 includes a light collecting optical member 1 and an antireflection film 2 disposed in a light-exiting surface of the light collecting optical member 1. The light collecting optical member 1 includes a light-entering surface IN1 (XZ-surface) on which incident light L1 is incident and a light-exiting surface OUT1 opposite to the light-entering surface IN1 and from which output light L10 is output, and the antireflection film 2 is disposed in the light-exiting surface OUT1. In the light collecting optical member illustrated in FIG. 1, the light-exiting surface OUT1 is a semi-cylindrical concave surface having a Z-axis as a central axis. Also, it is unnecessary for an opening angle of an arc about the central axis of the concave surface to be 180 degrees. Also, the antireflection film 2 is provided only in the concave surface in FIG. 1, but may be disposed in the whole surface of an XZ surface of the light exiting side in addition to the inside of the concave surface. Also, the antireflection film may be provided on the light-entering surface IN1.

A second metamaterial optical member 200 includes a light transfer member 1A and an antireflection film 2A disposed in an incident surface of the light transfer member 1A. A structure of the light transfer member 1A also includes an internal refractive index distribution and is the same as the light collecting optical member 1. The light transfer member 1A is different from the light collecting optical member 1 in that a function of dispersing light entered from a light-entering surface IN2 of the concave surface toward a light-exiting surface OUT2 is provided.

An object P is arranged between a pair of metamaterial optical members 100 and 200. When the device illustrated in FIG. 1 is a measuring device, the object P is a tube constituting a medium flow path. Various types of media FD within the tube flow. The incident light L1 from the light-entering surface IN1 of the first metamaterial optical member 100 is collected in a concave surface direction by the light collecting optical member 1 and externally exits from the light-exiting surface OUT1 via the antireflection film 2. The output light L10 is incident on the object P and transmitted through the object P and the light L20 is internally incident from the light-entering surface IN2 of the second metamaterial optical member 200 via the antireflection film 2A, travels while being diffused inside the light transfer member 1A, and is externally output as the light output light L2 from the light-exiting surface OUT2. Also, the light L20 includes transmitted light, scattered light, fluorescence, or the like.

In FIG. 1, the medium FD within the object P flows in the Z-axis direction. A direction in which the medium FD flows may be a vertical direction, or may be a horizontal direction.

Figure 2:
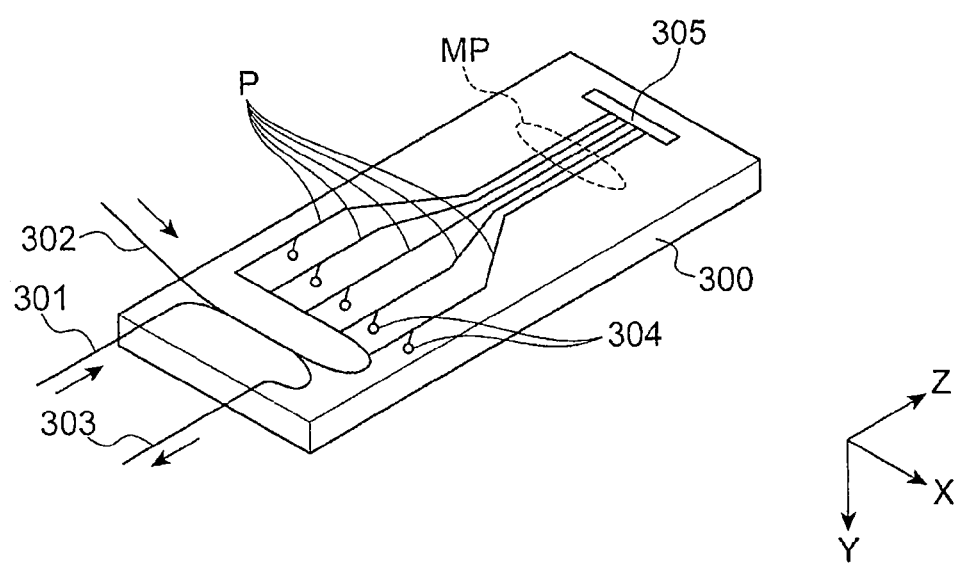
FIG. 2 is a perspective view of a medium introduction system including a plurality of medium flow paths.

FIG. 2 is a perspective view of a medium introduction system including a plurality of medium flow paths.

The measuring device can include a medium introduction system as illustrated in FIG. 2. In the medium introduction system, a plurality of medium flow paths (tubes) serving as objects P to be measured are arranged on a substrate 300 and the tubes include input tubes 301 and 302 for introducing media within the tubes and a medium output tube 303 for outputting an unnecessary part of a medium. For example, a medium to be measured is introduced into the tube 301 and a dilute solution is introduced into the tube 302.

A medium to be introduced includes an environmental hormone of ultra-fine particles (exogenous endocrine disrupting substance/exogenous endocrine disrupting chemical substance), blood or saliva collected from a living body, bacteria and viruses, or the like. According to a size or characteristics of a material to be inspected, the reaction with a specific reagent can be caused and it is also possible to add a labeling reagent such as a fluorescent label. In this device, it is possible to measure an amount of the influenza virus, O157, the bacteria salmonella, dioxin, a stress marker, or the like included in a liquid which flows within the medium flow path and determine the presence/absence thereof by detecting light transmitted through the medium. Inspection of blood glucose and lipid content can also be utilized for inspection of metabolic syndrome.

After the medium introduced into the tube is mixed with a dilute solution or a necessary liquid, the medium is mixed with a labeling reagent or a reaction reagent introduced from a reagent introduction unit 304, flows within the medium flow path, and reaches a detection unit MP. The detection unit MP detects light transmitted through the tube. A type of reagent may differ according to each of a plurality of medium flow paths. At an end of a tube through which the medium passing through the detection unit MP flows, a discharge unit 305 for absorbing a medium flowing within the tube or externally discharging the medium is provided. Also, inspection using a gas as the medium is also possible.

Figure 3:
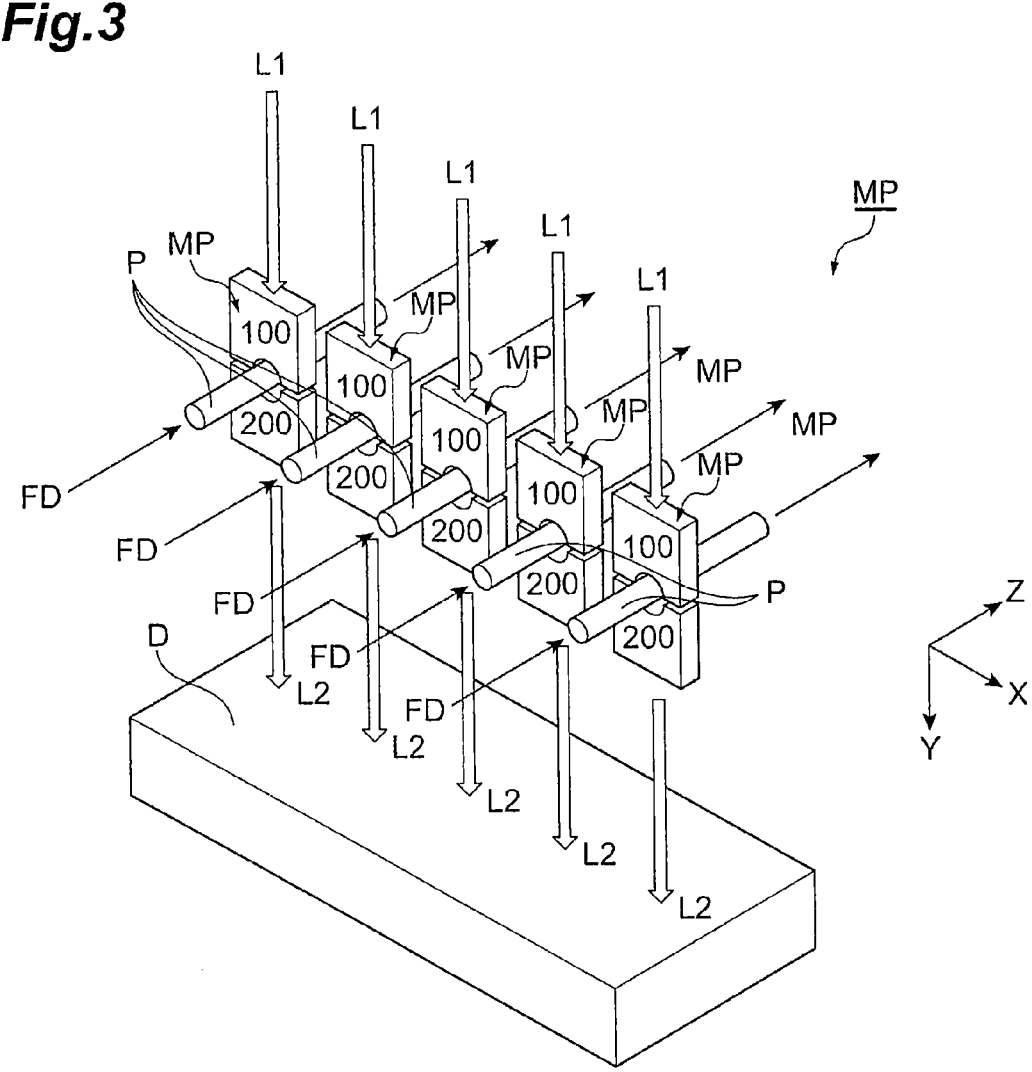
FIG. 3 is a perspective view of a measuring unit including a plurality of detection units.

FIG. 3 is a perspective view of a measuring unit including a plurality of detection units MP.

A structure of each detection unit MP is as illustrated in FIG. 1, but any structure other than that of FIG. 1 can be applied as long as a pair of metamaterial optical members are provided. A plurality of detection units MT are aligned in the X-axis direction and light L1 is incident on a light-entering surface of the metamaterial optical member 100 of an input side of each detection unit MP and passes through the inside of the object P and light L2 exits from the light-exiting surface of the metamaterial optical member 200 of the output side in the Y-axis direction. The output light L2 is detected by the light detector D arranged opposite to the light-exiting surface of the metamaterial optical member 200. A solid-state imaging element including a CCD image sensor or a MOS type image sensor can be used as the light detector D, but a plurality of photodiodes or photomultipliers for detecting the light L2 output from the detection units MP can also be used.

Because the object P is a medium flow path, the medium FD flows through the medium flow path and a signal according to characteristics of the medium FD flowing through each medium flow path is output from the detector D. Also, when the medium FD is a specific component of fluorescent labeled blood and the incident light L1 causes a fluorescent label to output light, the light L2 includes fluorescence and excited light according to an amount of the component. Thus, because it is possible to cut excited light by the second metamaterial optical member 200 by designing the second metamaterial optical member 200 according to a fluorescent wavelength, the light L2 exits from the light-exiting surface OUT2 of the second metamaterial optical member 200 can be set as only a fluorescent component. Also, an optical filter for selectively transmitting a fluorescent component may be arranged in a surface of the light detector D.

Also, because an intensity of the transmitted light L2 is reduced according to a particle mass when the medium FD includes particles in the liquid, a signal according to a characteristic (particle mass) of the medium FD flowing through each medium flow path is output from the light detector D.

Figure 4:
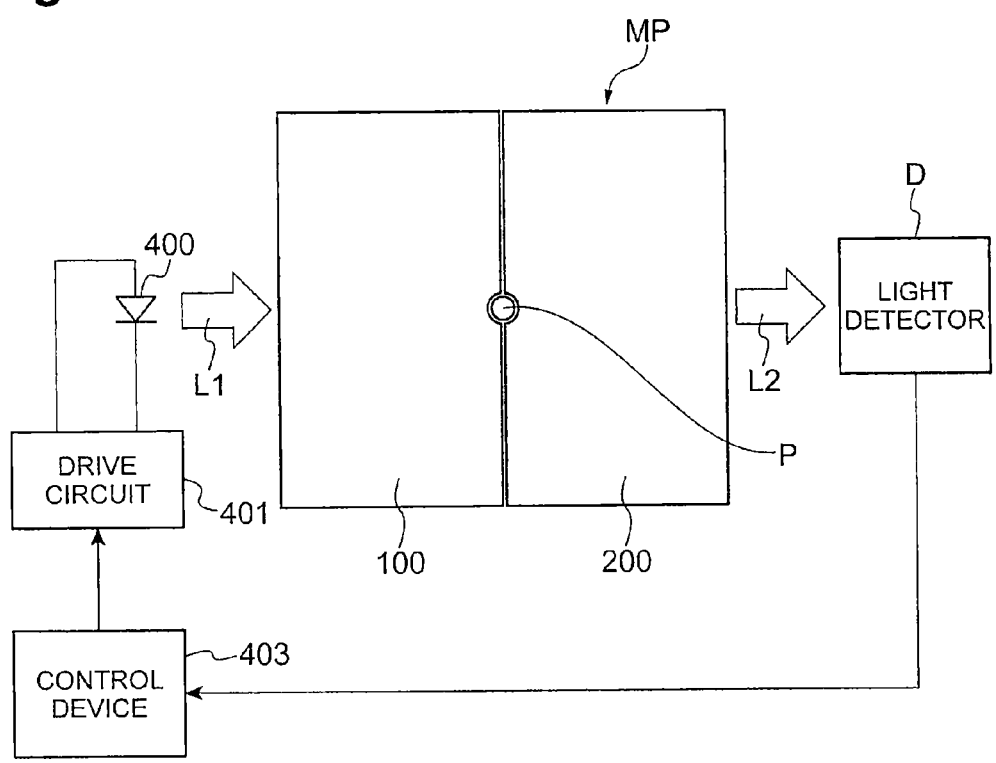
FIG. 4 is a block diagram of the measuring device.

FIG. 4 is a block diagram of the measuring device.

As described above, the object P is arranged between a pair of metamaterial optical members 100 and 200 and the light L2 passing through the object P is incident on the light detector D. An output signal of the light detector D is input to a control device 403 and stored within an internal storage device. The control device 403 is a computer, a control signal is output to the drive circuit 401, and a drive current is supplied from the drive circuit 401 to a light output element 400. The incident light L1 for the metamaterial optical member 100 of the detection unit MP is output from the light output element 400. The light output element is a laser diode, but a light emitting diode or the like can be used.

Figure 5:
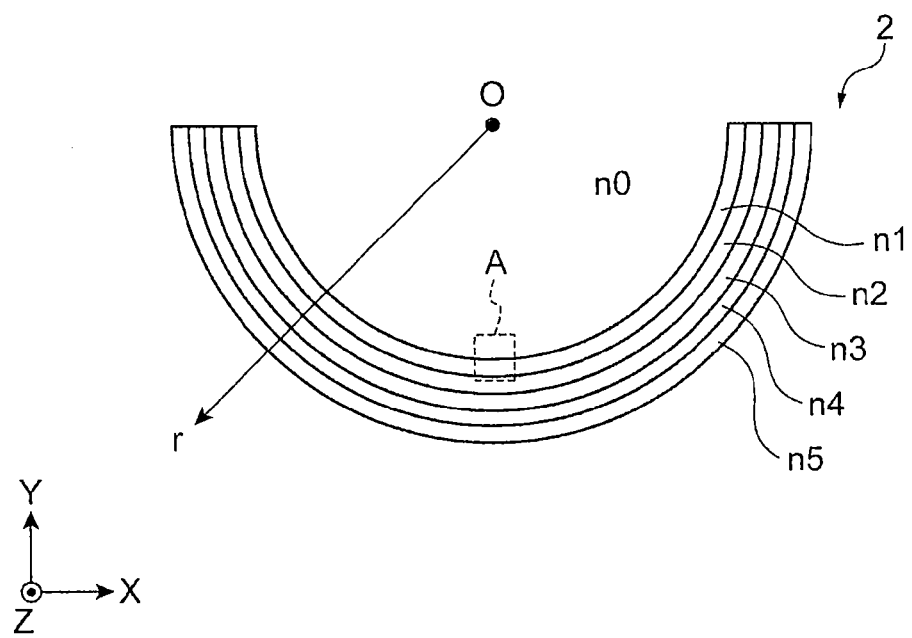
FIG. 5 is a plan view of an antireflection film in a metamaterial optical member.

FIG. 5 is a plan view of the antireflection film 2 in the metamaterial optical member 100 of the input side.

The antireflection film 2 has an arc shape within an XY-plane, and has a semi-cylindrical shape having the Z-axis as the central axis as the whole. The concave surface inside the antireflection film 2 constitutes a semi-cylindrical surface, but it is unnecessary for an opening angle of the arc of the XY-plane to be 180 degrees. The central axis of the arc is the Z-axis and a position of the central axis is set as the origin O within the XY-plane. When a distance r in a diameter direction of the arc from the origin O is defined, a refractive index distribution along the distance r from the origin O is as illustrated in FIG. 6.

Figure 6:
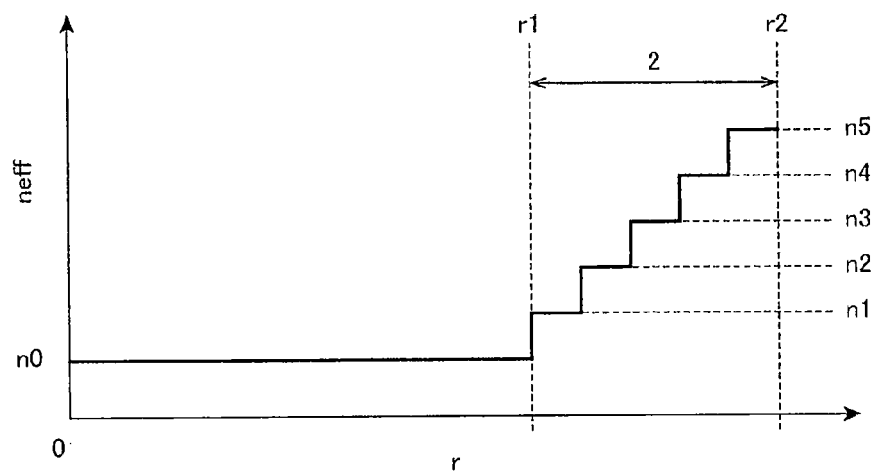
FIG. 6 is a graph illustrating a relationship between a distance r and an effective refractive index $n_{eff}$.

FIG. 6 is a graph illustrating a relationship between a distance r and an effective refractive index $n_{eff}$.

The antireflection film 2 is obtained by laminating layers of refractive indices n1, n2, n3, n4, and n5 from the inside as illustrated in FIG. 5. Also, for convenience, reference signs used for the layers n1 to n5 are the same as those of the refractive indices. As illustrated in FIG. 6, when the refractive index of an external gas (air in this example) is assumed to be n0, the refractive index within the antireflection film 2 gradually increases according to an increase of the distance r (n0<n1<n2<n3<n4<n5). Also, although the antireflection film 2 of this example has a five-step refractive index distribution, it is not limited to five steps as long as the antireflection film 2 has a refractive index distribution which changes in multiple steps.

Also, in FIG. 6, a position of a distance r1 is a position of an inner surface of the antireflection film 2 and a position of a distance r2 is a position of an outer surface of the antireflection film 2. The position of the distance r1 is set to 0, a direction from the distance r1 to the distance r2 is set as a positive direction, and the refractive index can change in multiple steps with a position L (µm) of a thickness direction of the antireflection film 2.

Figure 7:
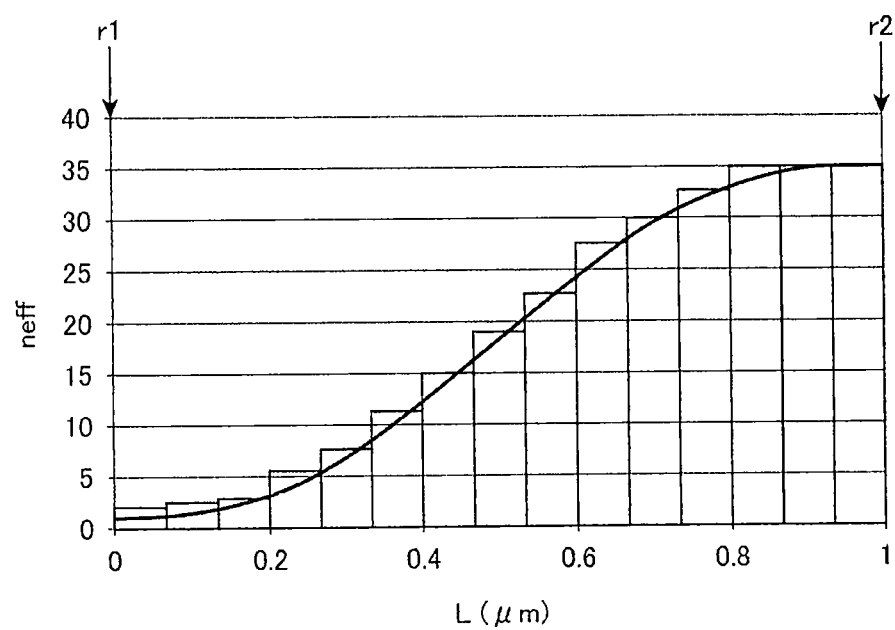
FIG. 7 is a graph illustrating a relationship between a position L (μm) and an effective refractive index $n_{eff}$ in an antireflection film.

FIG. 7 is a graph illustrating a relationship between a position L (µm) of the thickness direction and an effective refractive index $n_{eff}$ in the antireflection film 2.

In FIG. 7, a state in which an effective refractive index changes in L=0 to 1 µm is illustrated. This refractive index may gradually change or smoothly change continuously as indicated by a curve of FIG. 7.

Also, the refractive index distribution of the above-described antireflection film 2 gradually decreases in a stepwise shape or continuously in the traveling direction as described above, but the refractive index n at a distance t from the light-exiting surface OUT1 of the metamaterial optical member 1100 can be designated according to, for example, the following formula: $n=n0+(ns-n0)(10t^3-15t^4+6t^5)$. Here, n0 is a refractive index of a medium (air) of an outside and ns is a refractive index of the metamaterial optical member 100 in the light-exiting surface OUT1. The refractive indices in both the metamaterial optical member 100 and the antireflection films 2 can be 0 to 40.

Next, a method of forming a member having a desired refractive index will be described.

For example, a part of a region A of a first inner-side layer of the antireflection film 2 illustrated in FIG. 5 has a refractive index of n1. A layer having the refractive index n1 is obtained by arranging the region A in a direction perpendicular to the thickness direction of the antireflection film. Likewise, a layer having any refractive index can be configured by arranging a region having a desired refractive index in the direction perpendicular to the thickness direction.

The region having any refractive index can be configured as follows.

Figure 8:
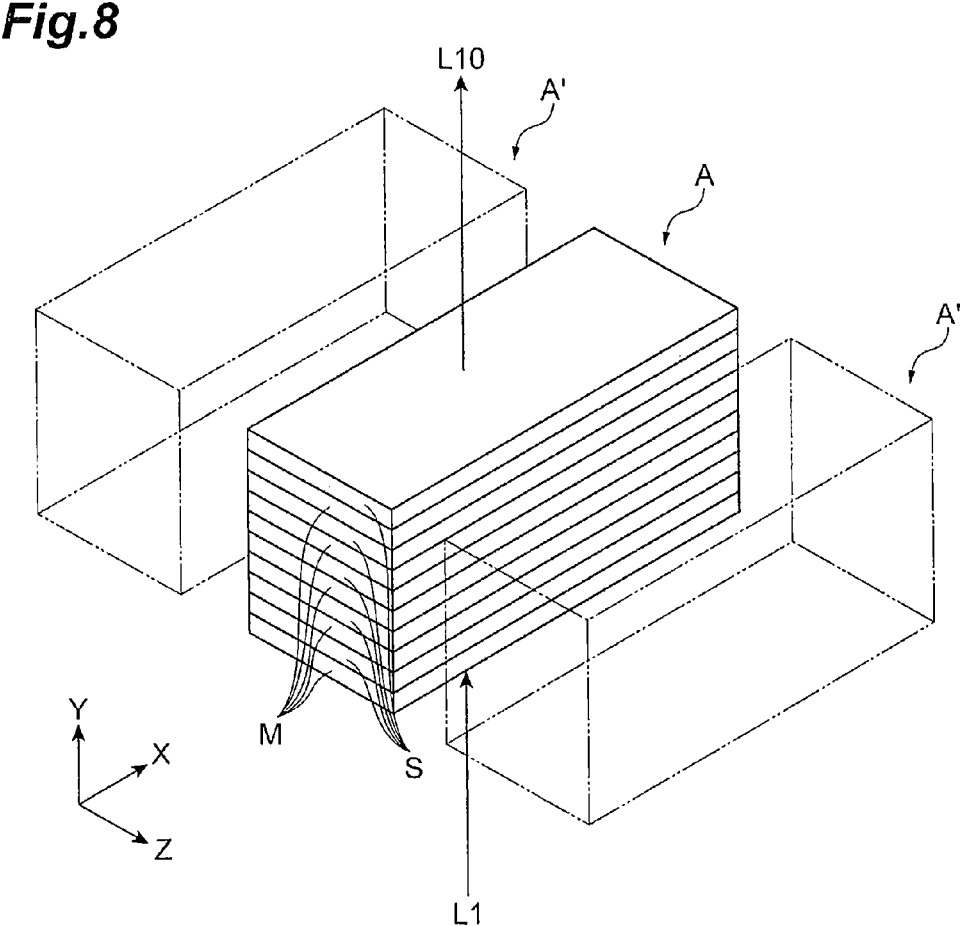
FIG. 8 is a perspective view illustrating a laminated structure in the antireflection film.

FIG. 8 is a perspective view illustrating a laminated structure of a partial region constituting a specific layer in the antireflection film 2, but for convenience of description, the above-described region A is representatively illustrated as the partial region. In the region A of FIG. 5, the thickness direction of the layer n1 is set as a Y-axis, directions perpendicular to the thickness direction are set as Z- and X-axes, and incident light can generally travel in the Y-axis direction.

The incident light L1 is incident on the region A and the output light L10 is assumed to be output. This laminated structure is obtained by alternately laminating layers having different materials. In this example, a metal layer (Ag) and a semiconductor layer (Ge) are alternately laminated. A thickness of one metal layer M is 4 nm and a thickness of one semiconductor layer S is 6 nm. An effective refractive index of the laminated structure including these materials depends upon dimensions of directions (Z- and Y-axes), but an average value of effective refractive indices in coordinate directions $n_{eff}=(n_x^2+n_y^2+n_z^2)^{1/2}$. That is, it is possible to adjust the refractive index by changing height and width dimensions of a structure formed in the region A.

Also, in FIG. 8, a state in which a region A' having the same structure as the region A having the laminated structure is arranged adjacent to the region A is illustrated.

Figure 9:
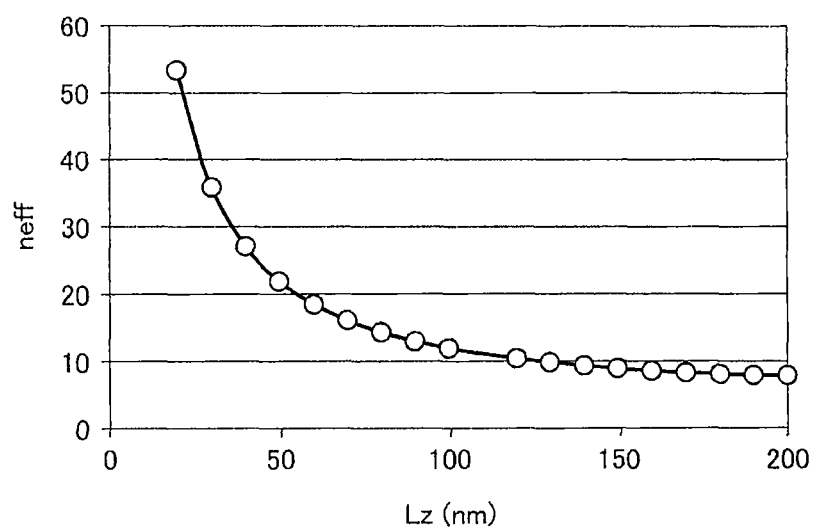
FIG. 9 is a graph illustrating a relationship between a dimension Lx in a length direction and the effective refractive index $n_{eff}$ in the laminated structure.

FIG. 9 is a graph illustrating a relationship between a dimension $L_Z$ in a length direction (Z-axis direction) and the effective refractive index $n_{eff}$ in the laminated structure of FIG. 8. Also, in this example, a dimension in a height direction (Y-axis direction) $L_Y=L_Z$ is assumed. That is, a shape of the light-exiting surface is a square. For example, when $L_Z=L_Y=30$ nm, the effective refractive index $n_{eff}=35.7$ can be set. A method of designing the refractive index and the permittivity as described above is disclosed in, for example, "J. Opt. Soc. Am. B, Vol. 29, No. 9, 2559 (2012)."

Figure 10:
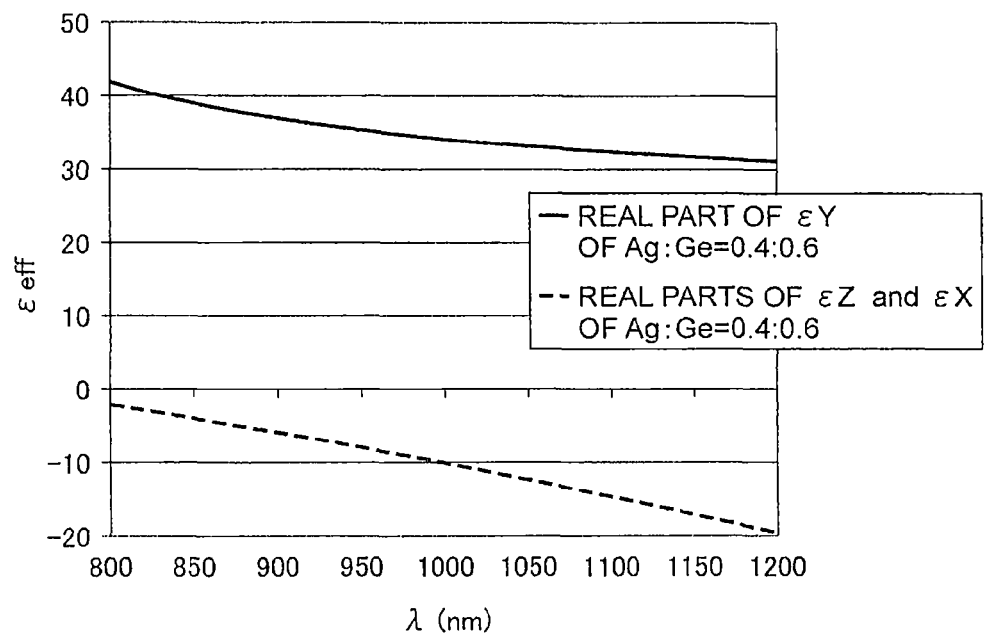
FIG. 10 is a graph illustrating a wavelength dispersion value of the main value of the permittivity tensor obtained from an effective medium theory when a volume ratio between silver and germanium is 0.4:0.6 in the laminated structure.

FIG. 10 is a graph illustrating a wavelength dispersion value of the main value of the permittivity tensor obtained from an effective medium theory when a volume ratio between silver and germanium is 0.4:0.6 in the laminated structure, and illustrates a relationship between a wavelength λ (nm) and effective permittivity $\varepsilon_{eff}$. When a volume ratio of Ag and Ge is set to 4:6, it can be found that both real parts of the effective permittivities $\varepsilon_Z$ and $\varepsilon_X$ of the Z- and X-directions are −9.8 and a real part of the effective permittivity $\varepsilon_Y$ of the Y-direction is 34.2 in the case of the wavelength λ=1 µm (=1000 nm). Also, $L_Z=L_Y=100$ nm is assumed.

Next, effects of the antireflection film 2 will be described.

First, the case in which no antireflection film 2 is disposed in the light collecting optical member 1 will be described.

Figure 11:
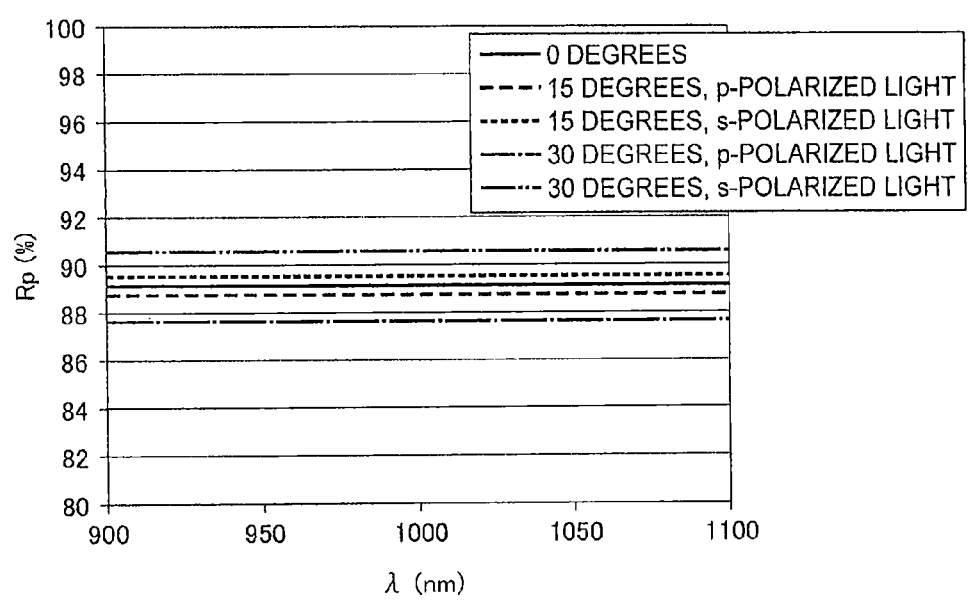
FIG. 11 is a graph illustrating a relationship between a wavelength λ of incident light and reflectivity Rp (%) when there is no antireflection film.

FIG. 11 is a graph illustrating a relationship between a wavelength λ of incident light and reflectivity Rp (%) when there is no antireflection film 2. In FIG. 11, angles of incidence of the incident light are assumed to be 0 degrees, 15 degrees, and 30 degrees and reflectivities of a p-polarized light component and an s-polarized light component included in the incident laser light are illustrated. Reflectivity in an interface when the refractive index in the light-exiting surface of the light collecting optical member is assumed to be 35 and an external gas is assumed to be air (refractive index=1) is shown in the graph. A constituent medium is assumed to be homogeneous and a wavelength distribution of the refractive index is assumed to be absent. At an angle of incidence of 0 degrees, the reflectivity is about 89% and a light of at least 87% or more is reflected even in the p-polarized light.

Next, the case in which the antireflection film 2 is disposed in the light collecting optical member 1 will be described.

Figure 12:
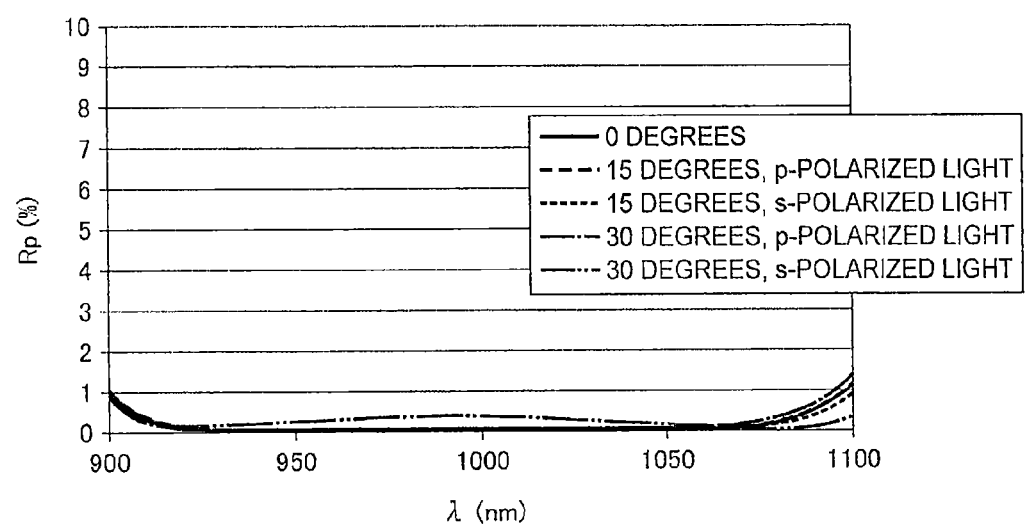
FIG. 12 is a graph illustrating a relationship between a wavelength λ of incident light and reflectivity Rp (%) when there is an antireflection film.

FIG. 12 is a graph illustrating a relationship between a wavelength λ of incident light and reflectivity Rp (%) when there is an antireflection film. In FIG. 12, angles of incidence of the incident light are assumed to be 0 degrees, 15 degrees, and 30 degrees and reflectivities of a p-polarized light component and an s-polarized light component included in the incident laser light are illustrated. The refractive index in the light-exiting surface of the light collecting optical member is 35 and an external gas is air (refractive index=1). A calculation method of this graph is similar to that described above.

At an angle of incidence of 0 degrees, the reflectivity is 1% or less, preferably 0.5% or less, in a range in which the wavelength 2 is at least 925 nm to 1075 nm regardless of a polarized light state. Also, the case in which this antireflection film includes a structure of six layers and the refractive index of a first layer=1.29 (thickness: 162 nm), the refractive index of a second layer=4.52 (thickness: 53.0 nm), the refractive index of a third layer=14.8 (thickness: 116 nm), the refractive index of a fourth layer=21.2 (thickness: 58.4 nm), the refractive index of a fifth layer=27.0 (thickness: 18.3 nm), and the refractive index of a sixth layer=29.5 (thickness: 8.45 nm) is shown.

Figure 13:
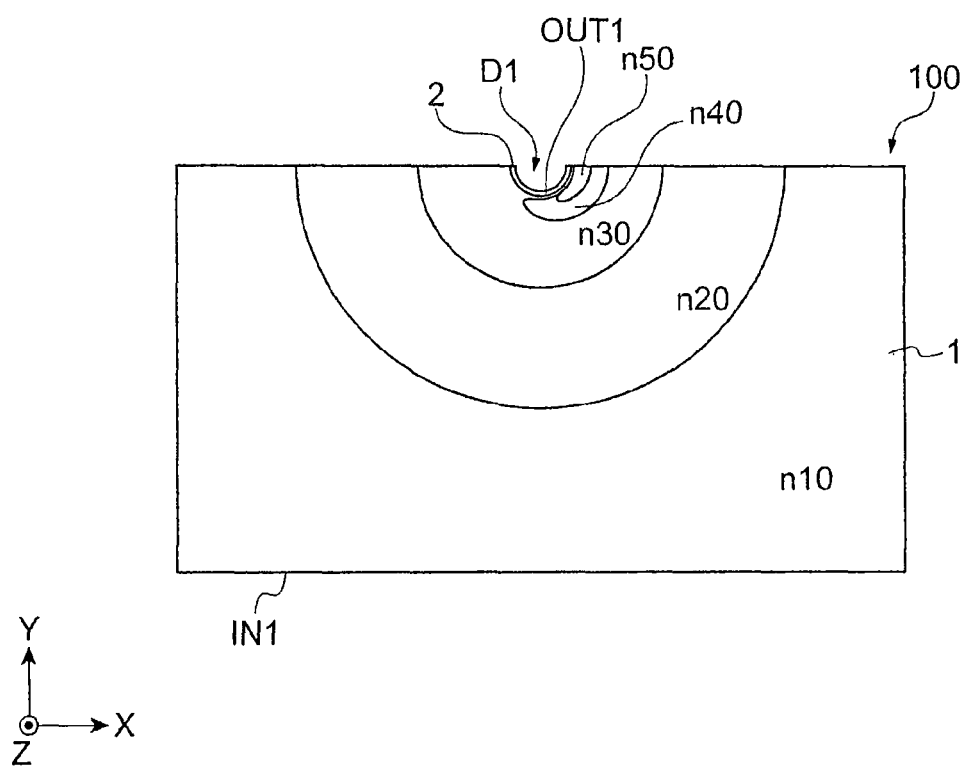
FIG. 13 is a plan view of a metamaterial optical member.

FIG. 13 is a plan view of the metamaterial optical member 100. The refractive index is set to increase from the light-entering surface IN1 to the light-exiting surface OUT1 in the XY-plane. That is, a region n50 having a high refractive index is around a concave portion D1 in which the antireflection film 2 is provided, a region n40 is positioned about the region n50, and regions n30, n20, and n10 are positioned to surround the regions n40 and n50 in order from the inside. Also, the refractive indices satisfy a relation of n50>n40>n30>n20>n10 and the refractive indices are average refractive indices within the regions. The refractive index is set to increase toward the concave portion D1 within each region.

A desired refractive index can be implemented using the above-described metamaterial structure illustrated in FIG. 8, or other structures can be adopted. Also, the refractive index distribution illustrated in FIG. 13 is referred to as a refractive index distribution of Hook.

Figure 14:
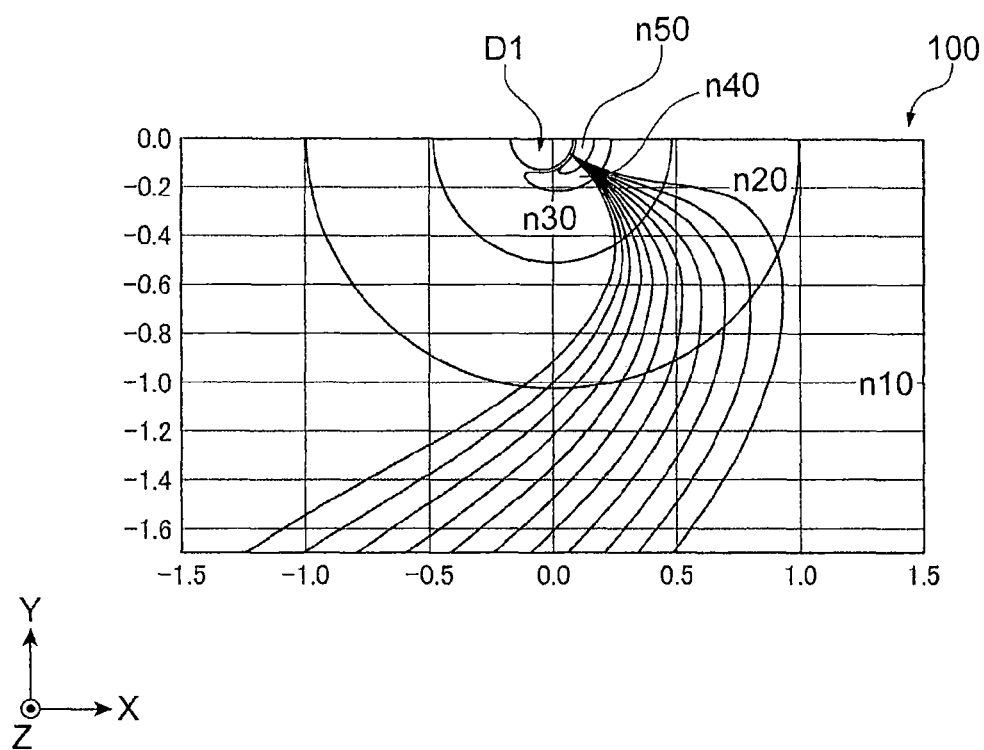
FIG. 14 is a diagram illustrating a path of light traveling within the metamaterial optical member of an input side.

FIG. 14 is a diagram illustrating a path of light traveling within the metamaterial optical member 100 of the input side illustrated in FIG. 13, and illustrates a graph overlapping a position of the metamaterial optical member. FIG. 14 illustrates a light propagation path when the angle of incidence of light is 45 degrees. Also, dimensions are indicated on a vertical axis and a horizontal axis and units of the dimensions are, for example, millimeters. Here, the dimension unit is not limited to millimeters, but may be centimeters, micrometers, or the like. Also, the illustration of the antireflection film is omitted.

After the incident light travels right in the drawing, the light is collected while being bent to the left side and collected in an inner surface of the concave portion D1 through the region n50 having a highest refractive index. Because the antireflection film (not illustrated) is provided at a light collection position, the collected light is externally output without being reflected by the interface.

Figure 15:
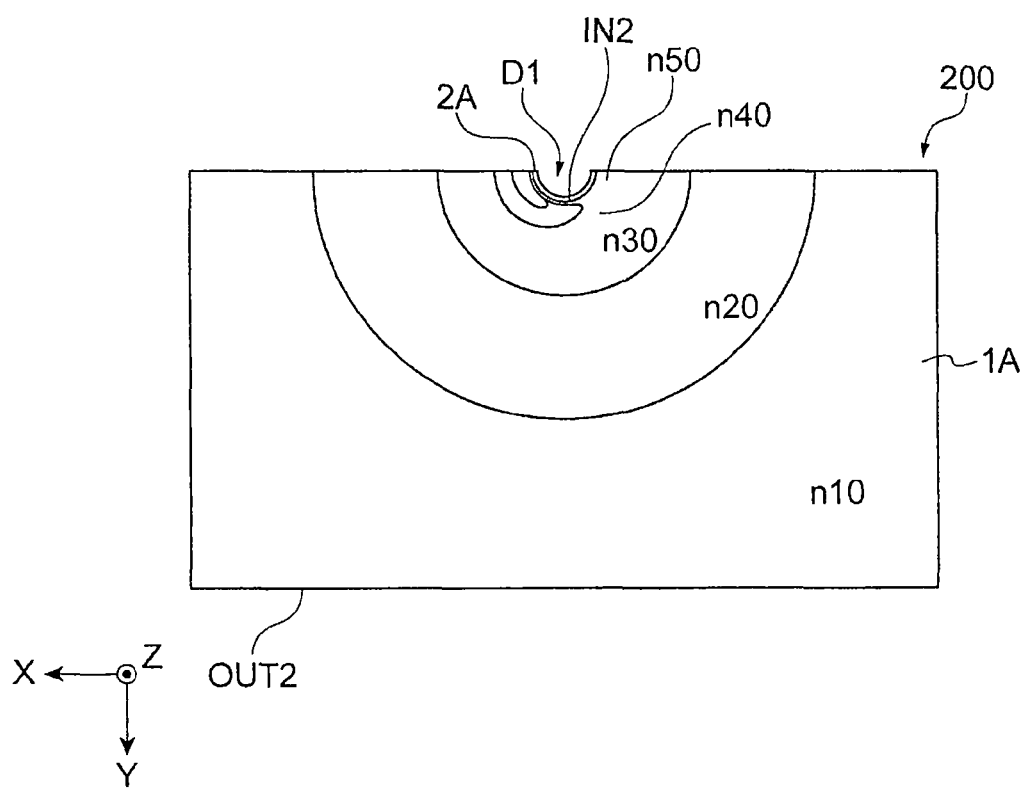
FIG. 15 is a plan view of the metamaterial optical member of an output side.

FIG. 15 is a plan view of the metamaterial optical member 200 of an output side.

The structure of the metamaterial optical member 200 of the output side is the same as the structure of the metamaterial optical member 100 of the input side, but is arranged at a symmetric position with respect to an axis of the object P illustrated in FIG. 1. Therefore, the metamaterial optical member 200 has a high refractive index around the concave portion D1, but a region having the highest refractive index is positioned at the left side of the drawing. Also, an antireflection film 2A is disposed in the light-entering surface IN2 serving as an inner surface of the concave portion D1.

Figure 16:
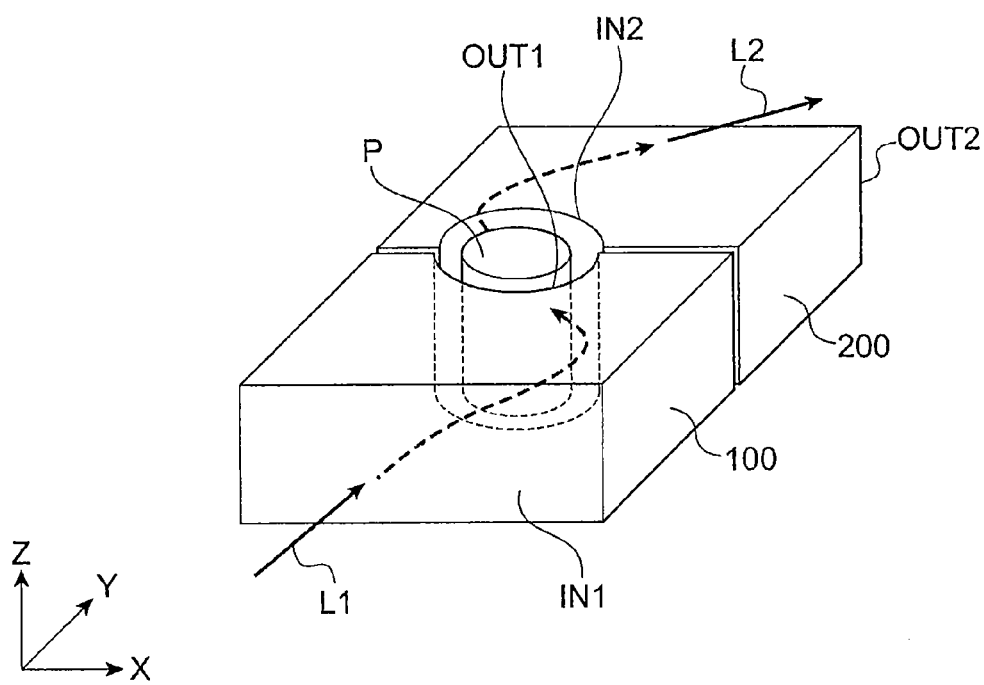
FIG. 16 is a diagram for describing a path of light passing through the detection unit of the measuring device.

FIG. 16 is a diagram for describing a path of light passing through the detection unit MP of the measuring device.

The incident light L1 is incident on the object P via the first metamaterial optical member 100 and the light transmitted through the object P is externally output as output light L2 via the second metamaterial optical member 200. A slight spacing is provided between the first metamaterial optical member 100 and the second metamaterial optical member 200 in FIG. 16, but they may be in contact. In this case, it is difficult for external light to be incident on the object P.

Figure 17:
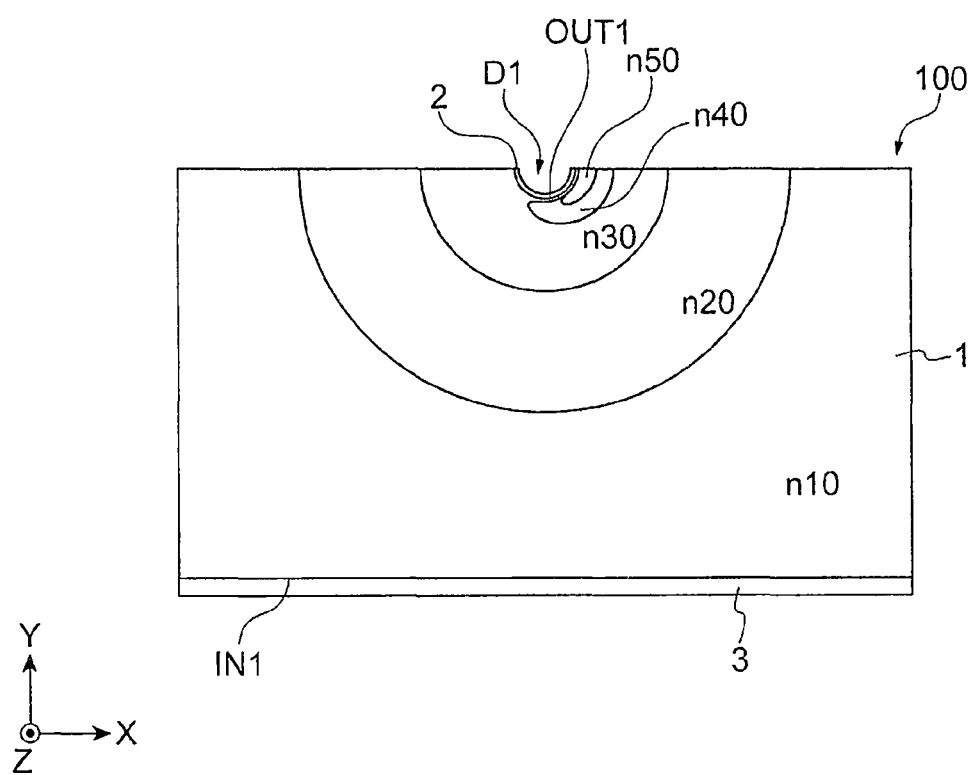
FIG. 17 is a plan view of a metamaterial optical member (improvement example) of an input side.

FIG. 17 is a plan view of a metamaterial optical member 100 (improvement example) of an input side.

This metamaterial optical member 100 is different from that illustrated in FIG. 13 only in that an antireflection film 3 is formed even on the light-entering surface IN1. In this case, it is possible to suppress interface reflection in the light-entering surface of the incident light for the metamaterial optical member 100.

Also, because the above-described antireflection film 3 is provided at a position at which a large refractive index change does not occur, the above-described antireflection film 3 may have a material of a general antireflection film. For example, a laminated structure in which any two types of films selected from a silicon oxide film, a titanium oxide film, a tantalum oxide film, a niobium oxide film, a hafnium oxide film, an aluminum oxide film, a magnesium fluoride film, etc. are alternately formed can be adopted as the structure of the antireflection film 3.

Figure 18:
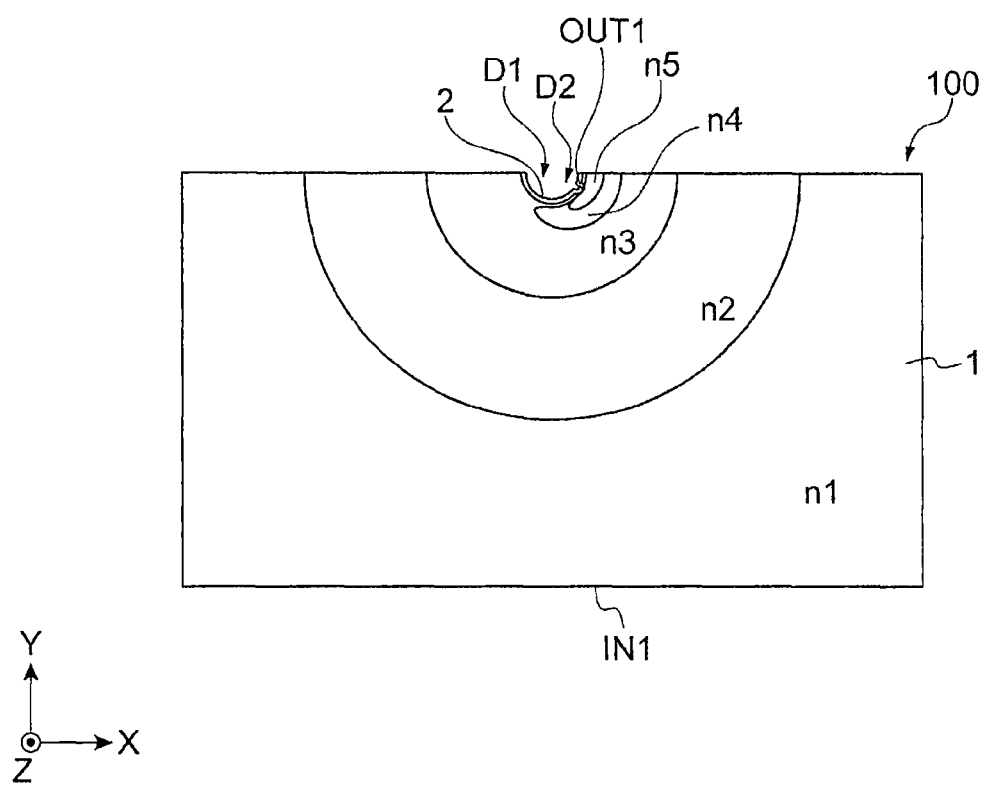
FIG. 18 is a plan view of a metamaterial optical member (modified example) of an input side.

FIG. 18 is a plan view of a metamaterial optical member 100 (modified example) of an input side.

This metamaterial optical member 100 is different from that illustrated in FIG. 13 only in that a concave portion D2 having a small curvature radius is further formed in an inner surface of the concave portion D1. The concave portion D2 has a semi-cylindrical surface having the Z-axis as the central axis and an opening angle of an arc within the XY-plane is 180 degrees, but the opening angle is not limited to 180 degrees.

Figure 19:
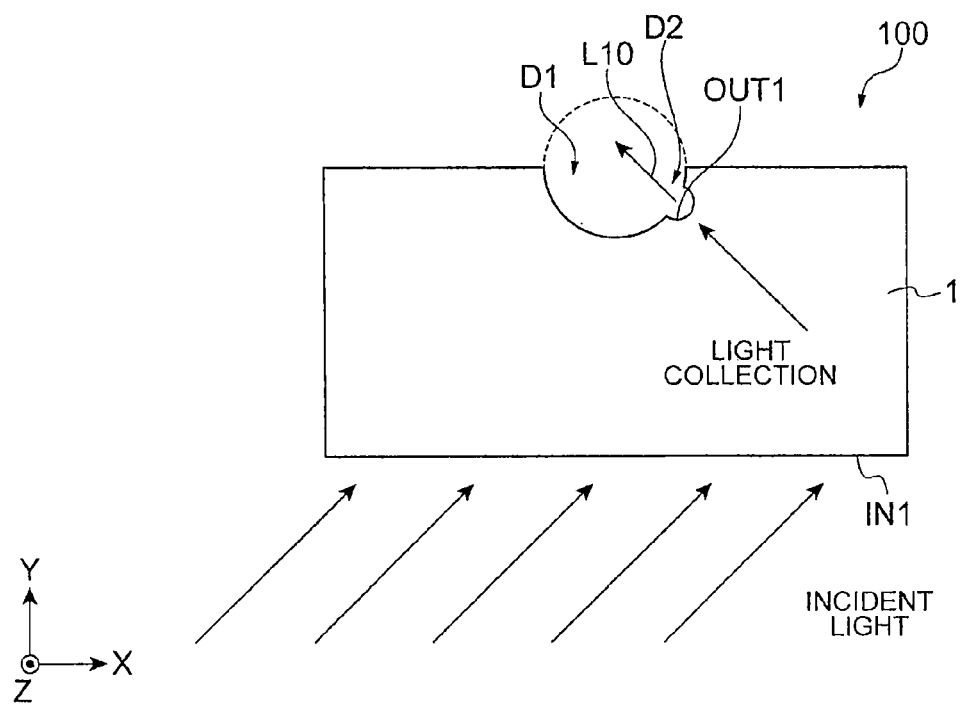
FIG. 19 is a diagram for describing traveling of light in the case of the structure of FIG. 18.

FIG. 19 is a diagram for describing traveling of light in the case of a structure of FIG. 18.

Also, the illustration of the antireflection film is omitted. Light entered from the light-entering surface IN1 to the inside of the light collecting optical member 1 is collected in a direction of the concave portion D1. In particular, the light is collected in the concave portion D2 positioned in an inner surface of the concave portion D1. It is possible to manufacture the concave portion D2 by removing a part of the concave portion D1 of the light collecting optical member 1 up to a region slightly in front of the light collection position. The concave surface of the concave portion D1 is an arc constituting a part of a circle within the XY-plane, but the concave surface of the concave portion D2 is also an arc constituting a part of a circle within the XY-plane. The collected light exits inside the concave portion D1 as output light L10 via the concave portion D2. It is only necessary for the antireflection film to be formed in an inner surface of the concave portion D2 related to at least light emission, but the antireflection film may be formed in the inner surface of the concave portion D1 or the whole surface opposite to the light-entering surface IN1.

As described above, the light-exiting surface OUT1 includes a concave surface (second concave surface) of the concave portion D2 continuous to a part of the concave surface constituting the concave portion D1 and having a smaller opening size than the concave surface of the concave portion D1. The opening size is defined by a length of a line segment connecting both ends of the arc within the XY-plane.

When the light collection position is positioned in a portion deeper in the light collecting optical member 1 than the concave surface of the concave portion D1, the second concave surface inside which the light collection position is positioned is partially provided. Because the second concave surface has a small opening size, the second concave surface can be formed even when a large part of the light collecting optical member 1 is not processed.

Next, other metamaterial structures capable of being adopted in the light collecting optical member 1 will be described. Also, it is possible to adopt the following metamaterial structures even in the antireflection film 2.

Figure 20:
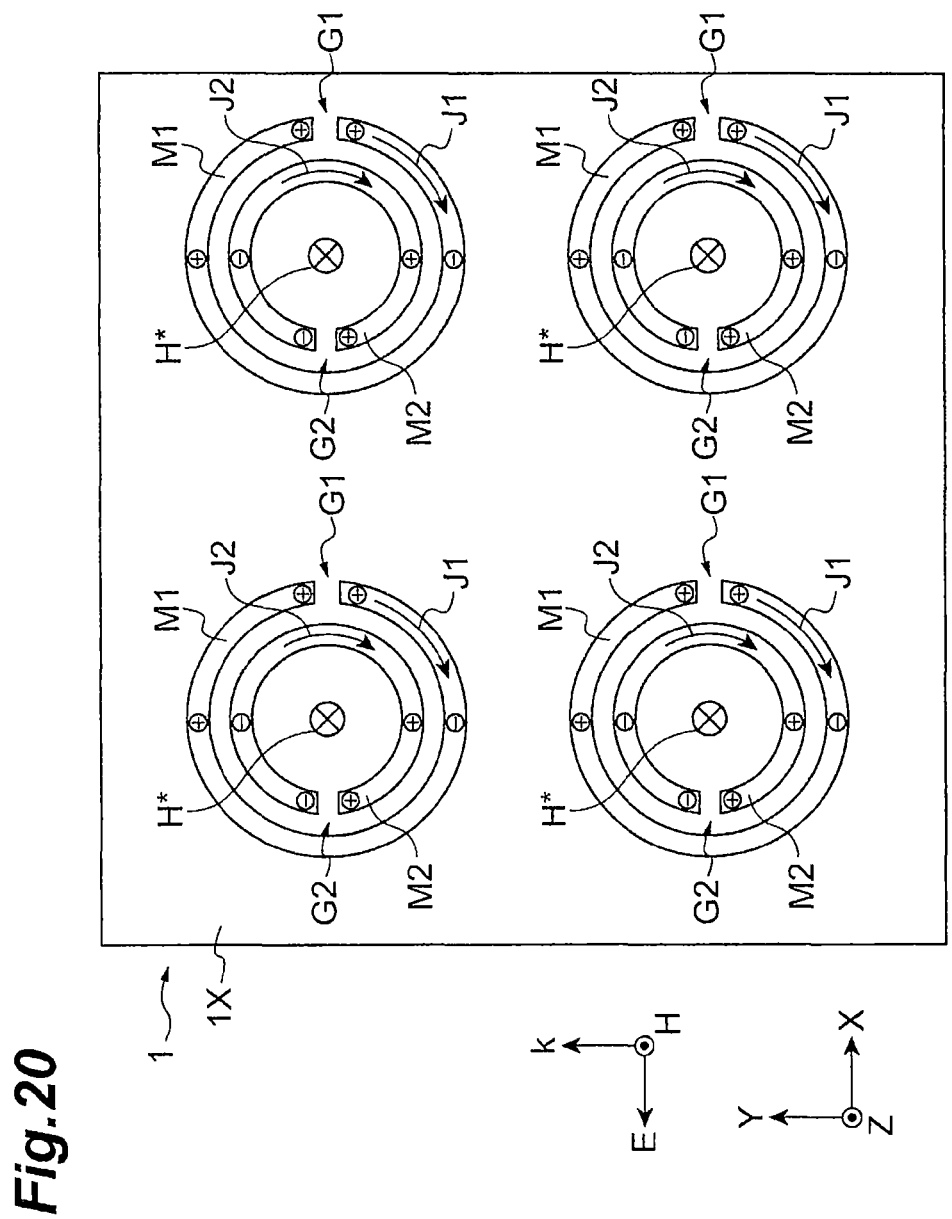
FIG. 20 is a plan view of a resonant metamaterial structure.

FIG. 20 is a plan view of a resonant metamaterial structure and illustrates a state of a partial region of the light collecting optical member 1.

When light is assumed to travel in the Y-axis direction and a traveling direction of the light is indicated by a wave number vector k, an electric field and a magnetic field are assumed to be generated in a direction perpendicular thereto. An electric field vector E and a magnetic field vector H are orthogonal to each other and both the electric field vector E and the magnetic field vector H are perpendicular to the wave number vector k. Also, because the directions of the vectors change according to the traveling of light, the refractive index is designed in the light collecting optical member 1 in consideration of the change. Also, in FIG. 20, the case in which the wave number vector k matches the Y-axis, the magnetic field vector H matches the Z-axis, and the electric field vector E is parallel to the X-axis is illustrated.

The light collecting optical member 1 has an insulator 1X including an insulating layer parallel to the XY-plane and rings M1 and M2 formed on the insulator 1X. The insulator 1X can be constituted of an inorganic insulator such as $SiO_2$ or $SiN_x$, or an organic material such as a resin can be used. The rings M1 and M2 are made of conductors and preferably made of metals. In FIG. 20, a pair of the rings M1 and M2 are partially cut and gaps G1 and G2 are formed in the cut part. When the magnetic field vector H is in the positive Z-axis direction, an opposite magnetic field H* is generated in the direction to cancel the magnetic field (the negative Z-axis direction) (Lenz's law). Currents J1 and J2 flow through the rings M1 and M2 made of the conductors, positive/negative charge is accumulated at both ends of the rings M1 and M2, and capacitors are formed in the gaps G1 and G2. Also, the capacitors are configured between the rings M1 and M2 of the outside and the inside.

Figure 21:
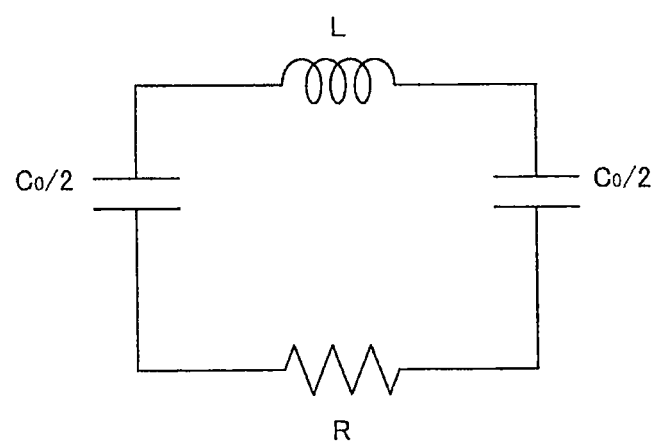
FIG. 21 is an equivalent circuit diagram of a resonant metamaterial structure.

FIG. 21 is an equivalent circuit diagram of a resonant metamaterial structure.

The metamaterial structure illustrated in FIG. 20 can be represented by a transmission circuit of FIG. 21. An LC resonance circuit including two capacitors having a capacitance of $C_0/2$, a coil having inductance L, and a coil having a resistance value R is configured. The coil is constituted of the rings M1 and M2.

Figure 22:
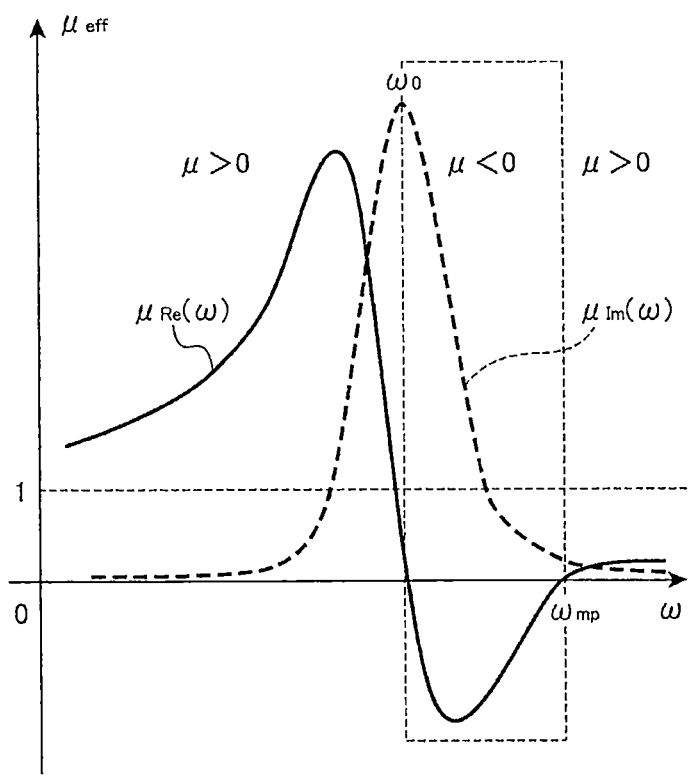
FIG. 22 illustrates a relationship between an angular frequency ω and permeability μ of incident light in the resonant metamaterial structure.

FIG. 22 illustrates a relationship between an angular frequency to and effective permeability $\mu_{eff}$ of incident light in the resonant metamaterial structure. Because a wavelength of light is $\lambda=2\pi c/\omega$ when a velocity of light is denoted by c and an angular frequency is denoted by $\omega$, an effective permeability $\mu_{eff}$ changes according to the wavelength $\lambda$ or the angular frequency $\omega$. In other words, when light having a wavelength $\lambda$ of a specific band is incident, resonance is generated and the permeability significantly changes. A solid line indicates a real part of the permeability $\mu_{Re}(\omega)$ in the case of a certain angular frequency $\omega$ and a dotted line indicates an imaginary part $\mu_{Im}(\omega)$. At a resonant angular frequency $\omega_0$, the imaginary part of the permeability $\mu$ is maximized and the real part becomes 0. When the angular frequency of light is higher than a resonant angular frequency $\omega_0$ and is less than $\omega_{mp}$, the real part of the permeability is negative, the imaginary part is positive, and the entire permeability $\mu<0$ is set. When the angular frequency of light is less than the resonant angular frequency $\omega_0$ or greater than $\omega_{mp}$, the real part of the permeability is positive, the imaginary part is negative, and the entire permeability $\mu>0$ is set.

Because the positive permeability (positive refractive index) is used in the present invention, it is preferable to use the angular frequency $\omega$ of light in a region of less than the resonant angular frequency $\omega_0$ and use incident light of a wavelength longer than a wavelength at which the resonant angular frequency $\omega_0$ is given. When inductance L and capacitance of a capacitor decrease in the LC resonance circuit, the resonant angular frequency $\omega_0$ increases. In other words, it can function as a material of different permeability (the refractive index $\propto$ the square root of the permeability) for light of the same wavelength $\lambda$ by controlling a resonant frequency $\omega_0$. Thus, it is possible to manufacture a metamaterial structure having a desired refractive index.

Also, a metal such as Au, Pt, Ag, Cu, Ti or Al, a nitride such as TiN, TaN, HfN, or ZrN, or a transparent conductive film such as ITO, ZnO:Al, ZnO:Ga, or the like can be preferably used as a material constituting a conductor of a metamaterial structure.

Although a metamaterial structure illustrated in FIG. 20 constitutes a split ring type resonator, a metamaterial structure including a rod pair array can also be adopted.

Figure 23:
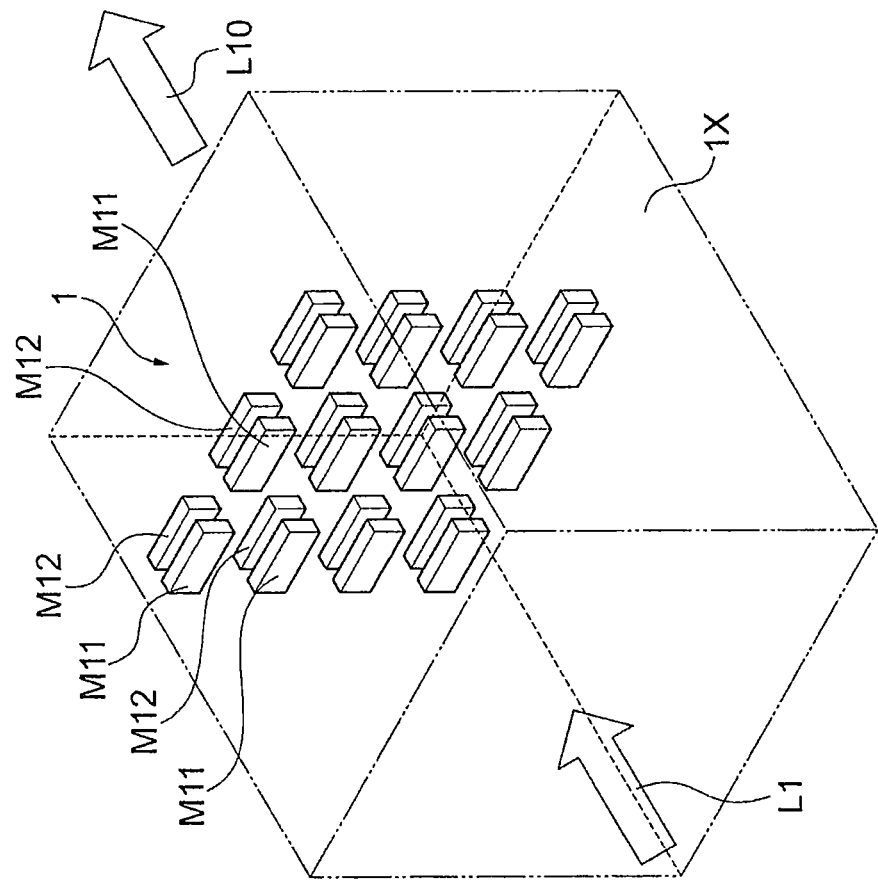
FIG. 23 is a perspective view of a metamaterial structure including a rod pair array.

FIG. 23 is a perspective view of a metamaterial structure including a rod pair array and illustrates a state of a partial region of the light collecting optical member 1.

This structure is obtained by changing the above-described split ring type ring shape to a pair of rods M11 and M12 opposite to each other within the light collecting optical member 1 and arranging a plurality of rod pairs. The rods M11 and M12 are constituted of conductors and their shapes are plate shapes, but they may have cylindrical or polygonal-prism shapes. The rods M11 and M12 are embedded in an insulator 1X.

A traveling direction of incident light L1 is set as the Y-axis, light travels along a wave number vector k, and a magnetic field vector H and an electric field vector E are orthogonal to the traveling direction of the light. Because the directions of the vectors change according to the traveling of the light, the refractive index is designed in the light collecting optical member 1 in consideration of the change. Also, in FIG. 23, the case in which the wave number vector k matches the Y-axis, the magnetic field vector H matches the Z-axis, and the electric field vector E is parallel to the X-axis is illustrated.

The rods M11 and M12 extend in the X-axis direction (the direction of the electric field vector E) and the rod pair is arranged in a two-dimensional shape within the XZ-plane. Also, the rod pair is arranged in the Y-axis direction, but its illustration is omitted. The incident light L1 is refracted by the rod pair and exits as output light L10.

Figure 24:
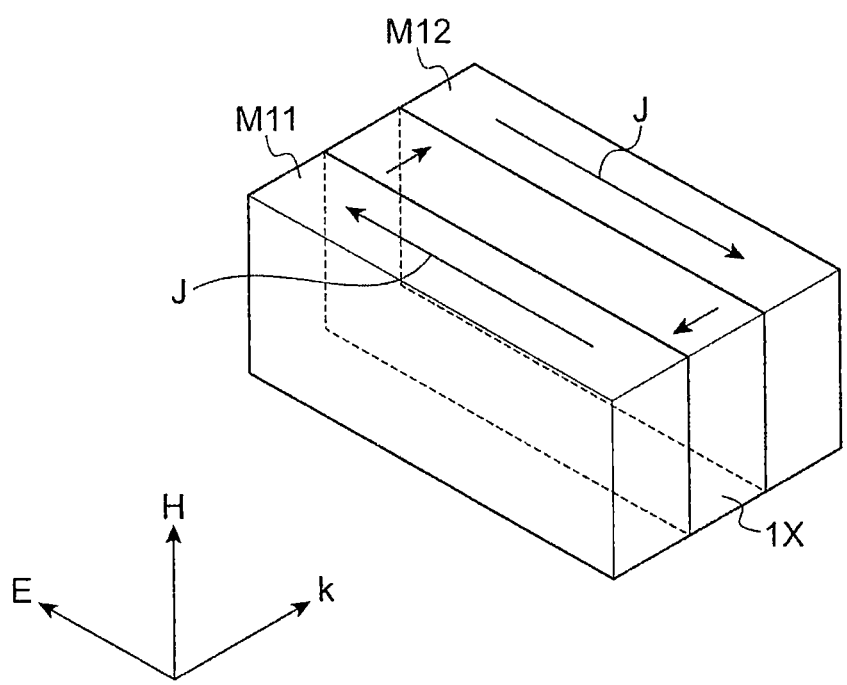
FIG. 24 is a diagram illustrating a current generated in the rod pair array.

FIG. 24 is a diagram illustrating a current generated in the rod pair array.

The insulator 1X is placed between the rod M11 and the rod M12. When light travels along the wave number vector k, the electric field vector E and the magnetic field vector H are generated in a direction perpendicular thereto. An opposite magnetic field is generated to cancel a magnetic field of a direction of the magnetic field vector H and a displacement current J flows in a direction of an arrow. Because an equivalent circuit of this structure can constitute an LC resonator, the refractive index can be controlled as in the split ring type resonator.

Figure 25:
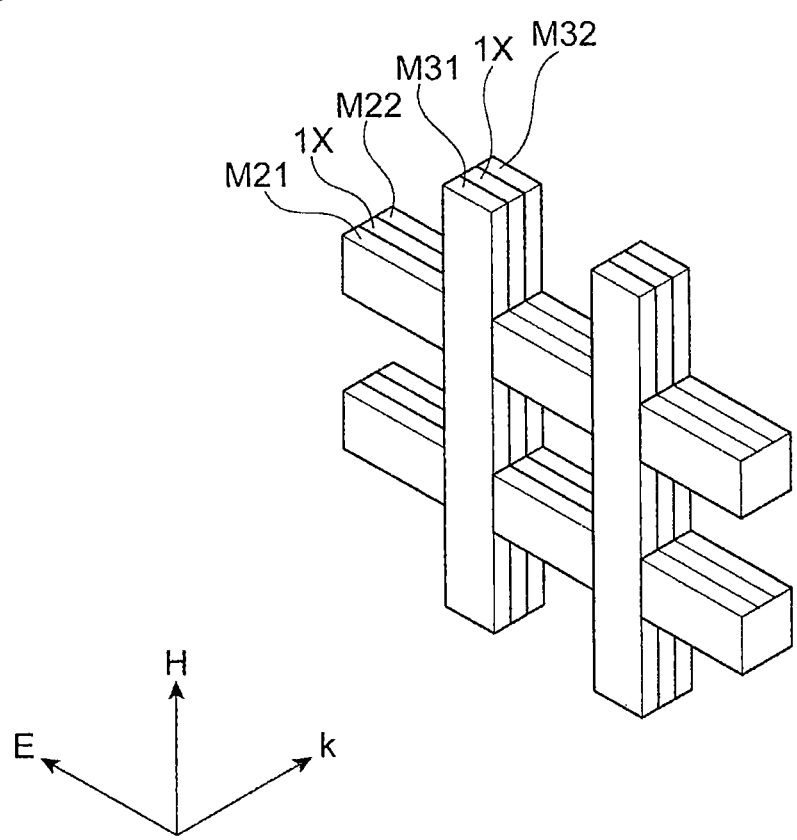
FIG. 25 is a perspective view of a reticulated metamaterial structure.

FIG. 25 is a perspective view of a reticulated metamaterial structure.

This metamaterial structure can also be regarded as a shape in which a rod pair array (rods M21 and M22) extending in the X-direction (corresponding to an E-direction) and the horizontal direction are located in addition to the rod pair array (rods M31 and M32) extending in the Z-direction (corresponding to an H-direction) and the vertical direction illustrated in FIG. 24. The insulator 1X is placed between the pair of rods M21 and M22 extending in the horizontal direction and between the pair of rods M31 and M32 extending in the vertical direction. Also, the rods M21 and M31 or the rods M22 and M32 are illustrated as separate materials for convenience of description in FIG. 25, but they may be integrated. In this case, the insulator 1X is arranged between reticulated conductors.

Because the rod pair array extending in the vertical direction can constitute an LC resonator as in the above-described split ring type resonator, the rod pair array is a structure responsive to a magnetic field, thereby controlling the permeability. Also, the rod pair array extending in the horizontal direction is a structure responsive to an electric field as in FIG. 8 described above and can control the permeability. Consequently, FIG. 25 illustrates a structure responsive to both an electric field and a magnetic field. When the structure of FIG. 25 is set as one "unit cell," it is possible to manufacture a structure which operates in a wide region (area) by arranging the unit cell in all directions. This structure is known a fish net structure because of its shape (Nature, vol. 455, p 376 (2008)). Because the unit cell is configured in a significantly small size of about ⅙ or less of an incident wavelength in these structures, it acts as atoms or molecules with respect to incident light. Thus, it is possible to transmit and refract light. The traveling direction of light is indicated by the wave number vector k and is perpendicular to both the electric field vector E and the magnetic field vector H.

Next, a type of device without a metamaterial optical member of the output side will be described.

In the device in which the metamaterial optical member of the output side is not used, light collected in the object P is incident, and thus an optical role ends. When the light detector is used as the object P, it can function as a light detection device for detecting light passing through the metamaterial optical member of the input side. When a laser medium is used as the object P, it can function as a laser excitation light source which collects excitation light passing through the metamaterial optical member of the input side to excite the laser medium and outputs a laser. Also, it is possible to configure a resonator by providing a mirror and a half-mirror at both ends of the laser medium.

Figure 26:
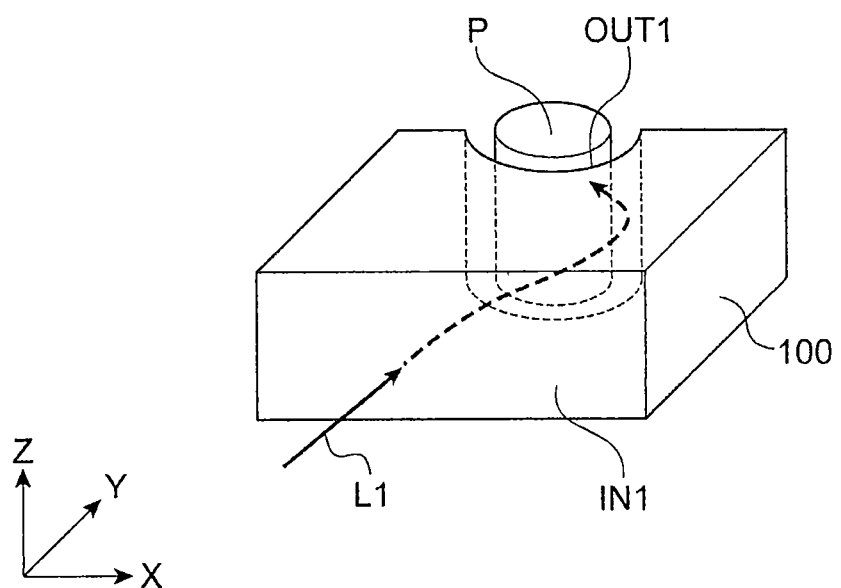
FIG. 26 is a diagram for describing a path of light entering an object in an execution device.

FIG. 26 is a diagram for describing a path of light irradiating an object in an execution device.

The object P has a columnar shape which can be arranged within the above-described concave portion. This device functions as a light detection device when the object P is a light detector and functions as a laser excitation light source when the object P is a laser medium. The incident light L1 for the metamaterial optical member 100 first travels in a direction of 45 degrees diagonally to the right, but the light travels after the direction of the light changes to the left from the middle and is collected to exit the inside of the concave portion and reach the object P.

As described above, an electric signal according to an intensity of incident light is output from the light detector when the incident light L1 is incident on the light detector and the laser medium is excited by the incident laser light in the case of the laser medium.

Figure 27:
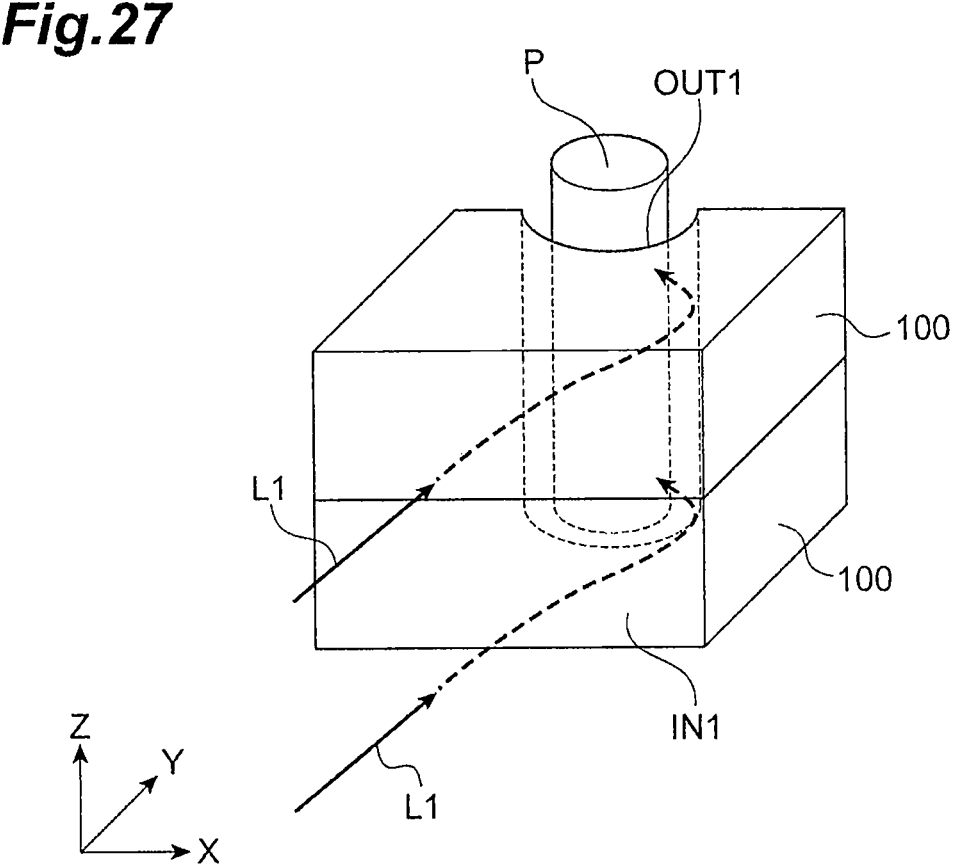
FIG. 27 is a diagram for describing a path of light entering an object in the execution device.

FIG. 27 is a diagram for describing a path of light irradiating an object in the execution device.

This structure is obtained by stacking two metamaterial optical members 100 in the Z-axis direction in the execution device illustrated in FIG. 26. In the case of this structure, it is possible to cause the incident light L1 to be incident on the object P even when the dimension in the Z-axis direction of the object P increases. The operation and effect of this device are the same as those of the device illustrated in FIG. 26. Because the metamaterial optical member 100 is arranged in the vertical direction, a line sensor can be used as the light detector and it can also be used as a multi-wavelength excitation light source by piling up a plurality of types of elements as the laser medium.

Figure 28:
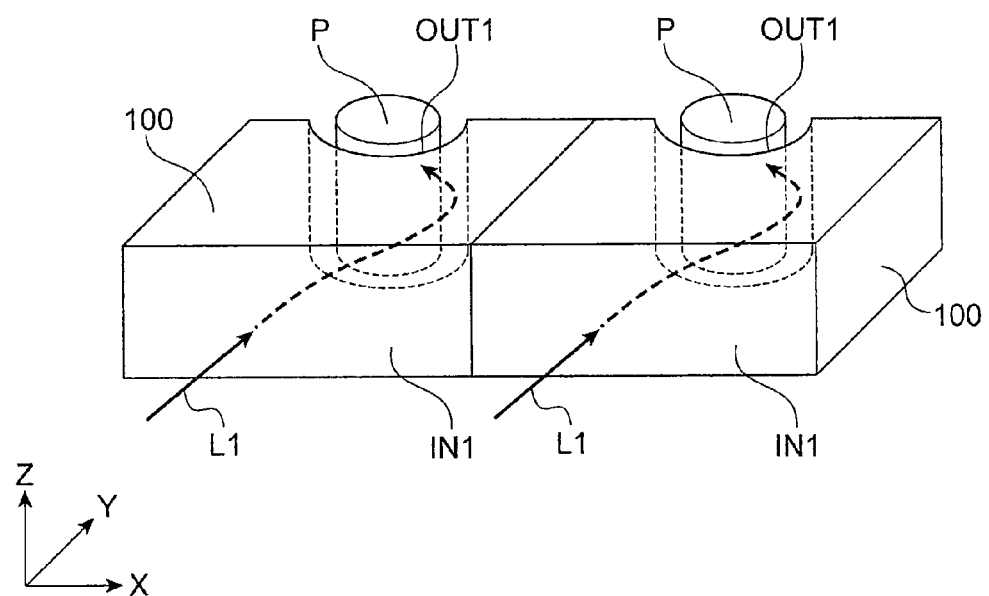
FIG. 28 is a diagram for describing a path of light entering an object in the execution device.

FIG. 28 is a diagram for describing a path of light irradiating an object in the execution device.

This structure is obtained by stacking two metamaterial optical members 100 in the X-axis direction in the execution device illustrated in FIG. 26. In the case of this structure, it is possible to cause the incident light L1 to be incident on the object P even when the number of objects P is two. The operation and effect of this device are the same as those of the device illustrated in FIG. 26. A plurality of line sensors, etc. can be used as a plurality of objects P.

Figure 29:
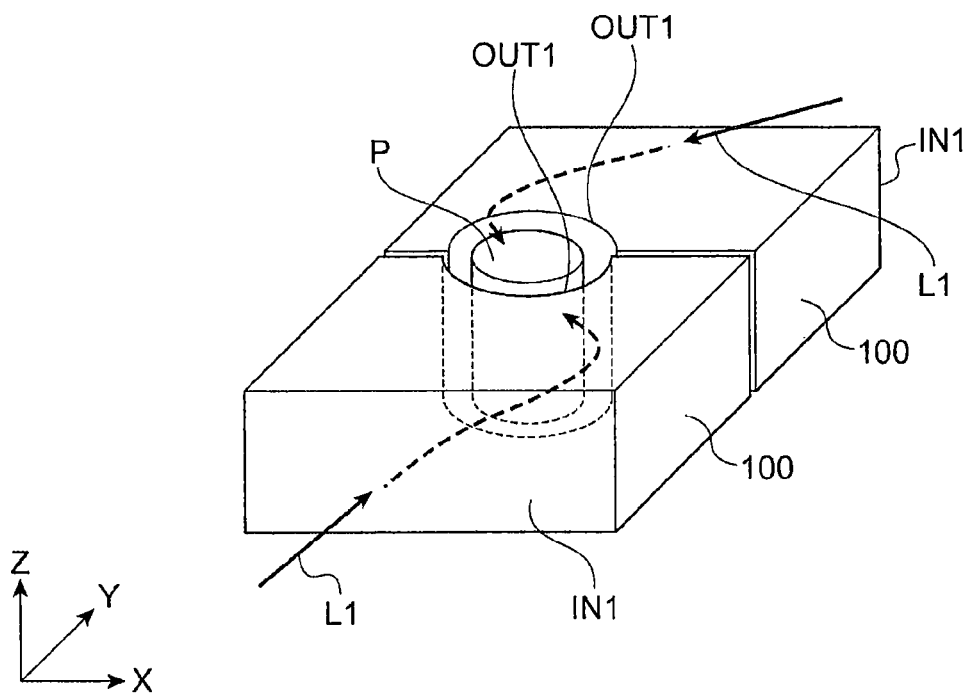
FIG. 29 is a diagram for describing a path of light entering an object in the execution device.

FIG. 29 is a diagram for describing a path of light irradiating an object in the execution device.

This structure is obtained by stacking two metamaterial optical members 100 in the Y-axis direction in the execution device illustrated in FIG. 26, sandwiching the object P between the two metamaterial optical members 100, and causing incident light L1 to be incident from different directions within the object P. In the case of this structure, high-density incident light L1 can be input to the object P. The operation and effect of this device are the same as those of the device illustrated in FIG. 26.

Figure 30:
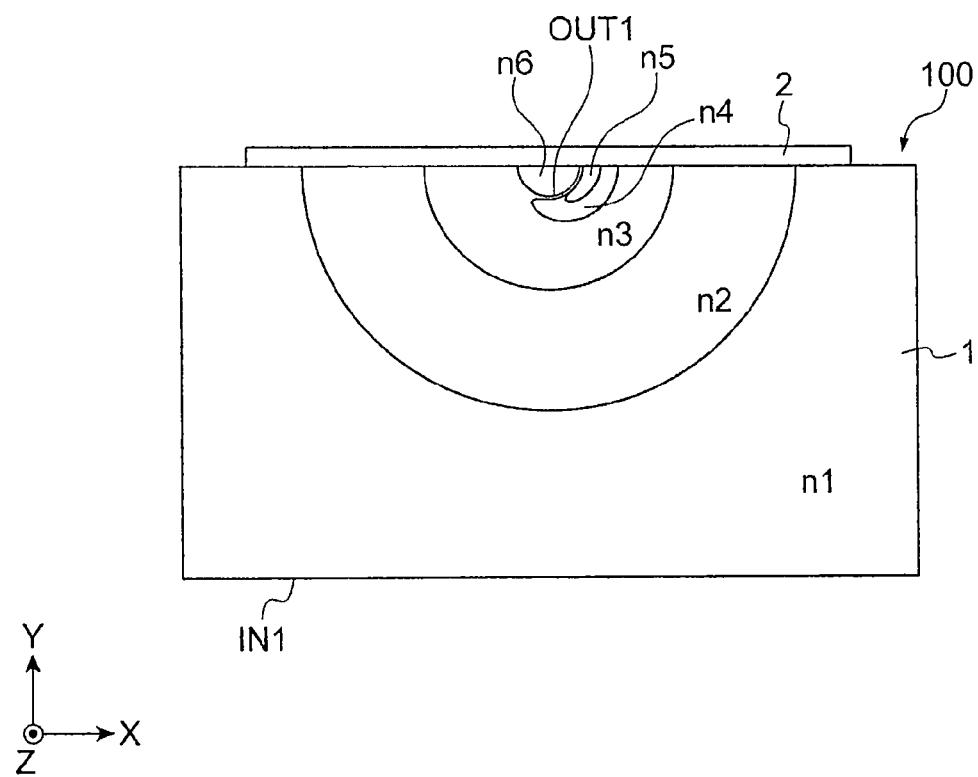
FIG. 30 is a plan view of a metamaterial optical member in which a light-exiting surface is of a flat type.

FIG. 30 is a plan view of a metamaterial optical member in which a light-exiting surface is of a flat type.

The metamaterial optical member 100 is different from that illustrated in FIG. 13 in that no concave portion is disposed in the metamaterial optical member 100, the light-exiting surface OUT1 is a flat surface, and the antireflection film 2 is disposed in a surface including the light-exiting surface OUT1, and the remaining configuration is the same. Because the flat surface is used in the light-exiting surface, a region n6 having a high refractive index is disposed in a region in which the concave portion is located in FIG. 13. The region n6 is positioned inside a region n5 and their refractive indices satisfy n5<n6. Also, for convenience of description, the regions and the refractive indices are denoted by the same reference signs.

Because the region n6 has a highest refractive index in the metamaterial optical member 100, light entered from the light-entering surface IN1 passes through the inside of the metamaterial optical member 100 and is collected in the light-exiting surface OUT of the region n6. The light collected in the light-exiting surface OUT1 externally exits through the antireflection film having the refractive index which gradually decreases in the positive Y-axis direction. A gas (air) is in the outside. Also, the region n6 may be a region having a given high refractive index, or may have a refractive index distribution in which the refractive index gradually increases in the light collection direction.

Also, even in the structure of the light-exiting surface OUT1, it is possible to adopt a similar combination to the case of the structure having the concave portion. That is, the antireflection film can be provided even in the light-entering surface side, the application to various types of device is possible, or a plurality of metamaterial optical members 100 can be combined.

Figure 31:
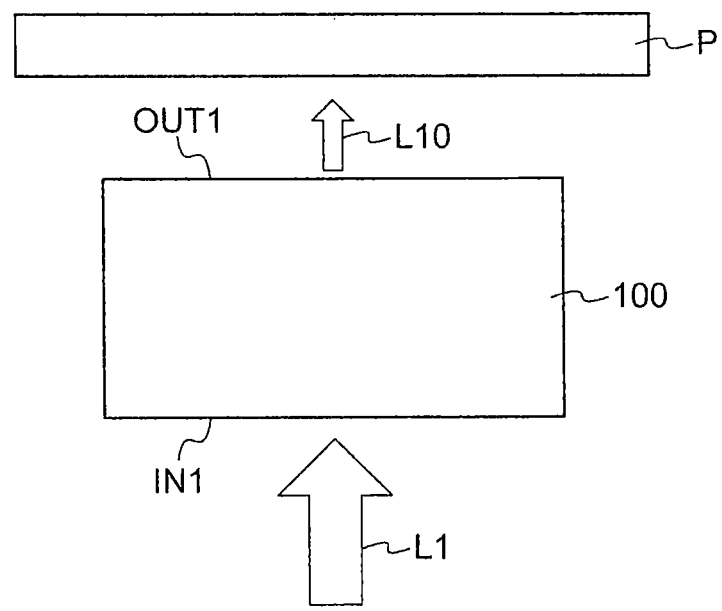
FIG. 31 is a diagram illustrating a relationship between the metamaterial optical member and an object.

FIG. 31 is a diagram illustrating a relationship between the metamaterial optical member and an object.

Light L1 incident from the light-entering surface IN1 of the metamaterial optical member 100 passes through the inside and exits from the light-exiting surface OUT and the light L10 transmitted through the metamaterial optical member 100 reaches the object P. The metamaterial optical member 100 and the object are adhered closely to each other or separated from each other. As the shape of the object P, a plate shape that can easily be opposite to a flat surface can be used in addition to the columnar shape capable of being arranged within the above-described concave portion. The object P may be a physically integral solid or a plurality of elements which are separated from each other.

When the object P is a plate-shaped light detector, a solid-state imaging element such as a CCD image sensor or a MOS image sensor can be used as the light detector. A line sensor may be used as the solid-state imaging element in addition to a two-dimensional image sensor.

Figure 32:
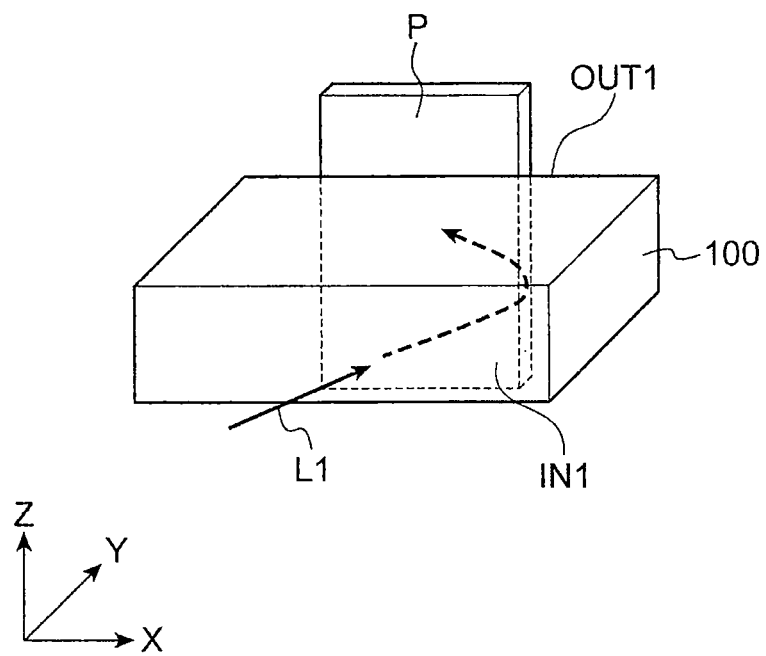
FIG. 32 is a diagram for describing a path of light entering an object in the execution device.

FIG. 32 is a diagram for describing a path of light irradiating an object in the execution device.

When the object P has a plate-like shape and the light-exiting surface OUT1 of the metamaterial optical member 100 is a flat surface, the object P can be easily arranged for the metamaterial optical member 100. This device functions as the light detection device when the object P is a light detector and functions as the laser excitation light source when the object P is a laser medium. The incident light L1 for the metamaterial optical member 100 travels in a direction of 45 degrees diagonally to the right, but the light travels after the direction of the light changes to the left from the middle and is collected to exit the inside of the concave portion and reach the object P.

As described above, an electric signal according to an intensity of incident light is output from the light detector when the incident light L1 is incident on the light detector and the laser medium is excited by the incident laser light in the case of the laser medium.

Figure 33:
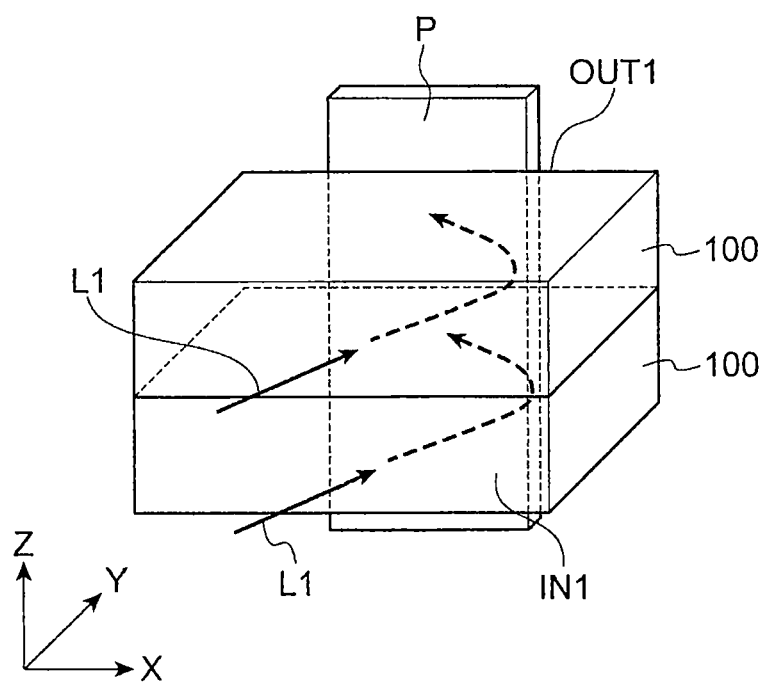
FIG. 33 is a diagram for describing a path of light entering an object in the execution device.

FIG. 33 is a diagram for describing a path of light irradiating an object in the execution device.

This structure is obtained by stacking two metamaterial optical members 100 in the Z-axis direction in the execution device illustrated in FIG. 32. In the case of this structure, it is possible to cause the incident light L1 to be incident on the object P even when the dimension in the Z-axis direction of the object P increases. The operation and effect of this device are the same as those of the device illustrated in FIG. 32. Because the metamaterial optical member 100 is arranged in the vertical direction, a line sensor can be used as the light detector and it can also be used as a multi-wavelength excitation light source by piling up a plurality of types of elements as the laser medium.

Figure 34:
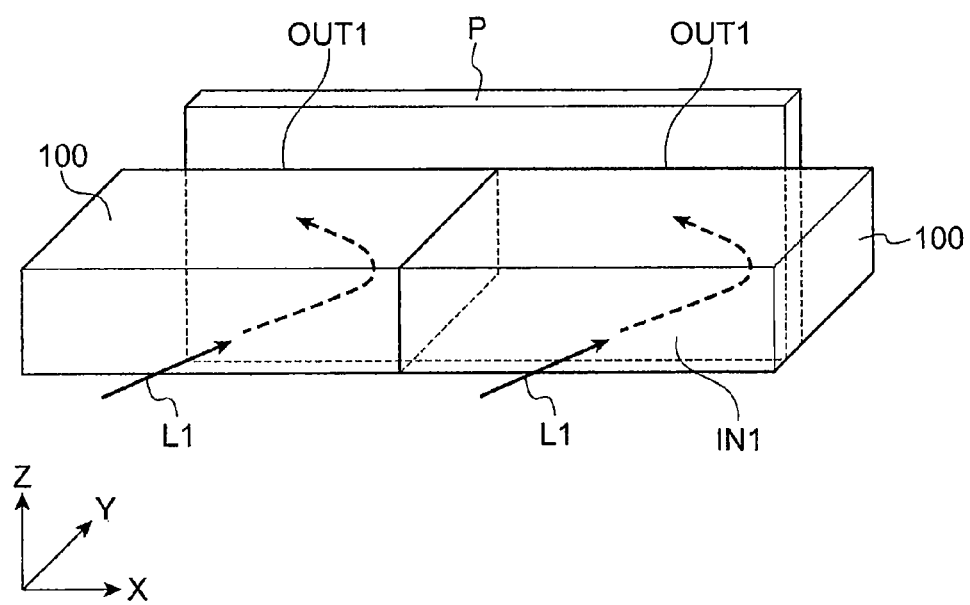
FIG. 34 is a diagram for describing a path of light entering an object in the execution device.

FIG. 34 is a diagram for describing a path of light irradiating an object in the execution device.

This structure is obtained by arranging two metamaterial optical members 100 in the X-axis direction in the execution device illustrated in FIG. 32. In the case of this structure, it is possible to cause the incident light L1 to be incident on the object P even when a dimension of the object P in the X-axis direction increases or the number of objects P increases to two or more. The operation and effect of this device are the same as those of the device illustrated in FIG. 32. A line sensor extending in the X-axis direction, etc. can be used as the object P.

Figure 35:
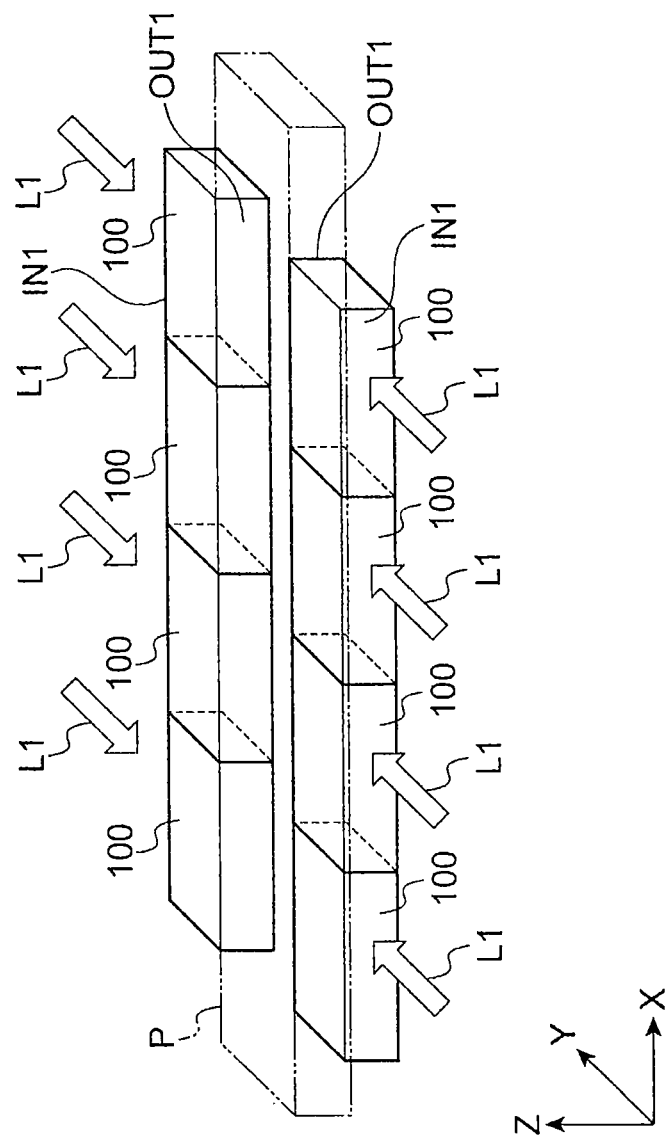
FIG. 35 is a perspective view of the execution device.

FIG. 35 is a perspective view of the execution device.

This structure is obtained by arranging two metamaterial optical members 100 in the X-axis direction in the execution device illustrated in FIG. 32, sandwiching both ends of the object P in the Y-axis direction between the two metamaterial optical members 100, and causing incident light L1 to be incident from different directions within the object P. In the case of this structure, higher-density incident light L1 can be input to the object P. The operation and effect of this device are the same as those of the device illustrated in FIG. 32. The shape of the laser medium is a rectangular solid extending in the X-axis direction when the object P is a laser medium and the metamaterial optical member 100 is arranged in proximity to two XZ-planes opposite to each other. A laser excitation light source including this structure can also be used as a driver for laser nuclear fusion. In this case, an excitation laser (wavelength of 804 nm) can be used as the incident light L1 and HAP4 (Nd-doped phosphate glass) can be used as the laser medium.

Figure 36:
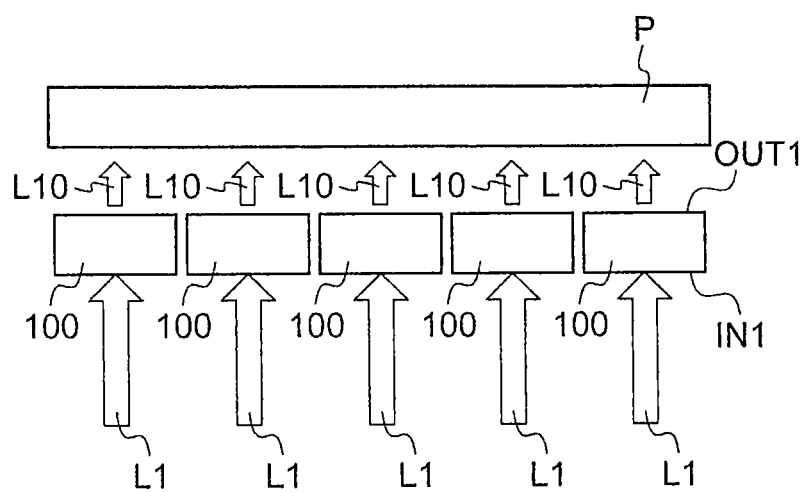
FIG. 36 is a diagram for describing a path of light entering an object in a light detection device.

FIG. 36 is a diagram for describing a path of light irradiating an object in a light detection device.

In this light detection device, a plurality of metamaterial optical members 100 are opposite to the object P and arranged in a line. In the present example, the object P is a line sensor. In this case, according to an intensity of light L1 incident on each metamaterial optical member 100, the collected light L10 emits from the metamaterial optical member 100 and incident on the line sensor. Signals of one-dimensionally distributed optical images are output from the line sensor.

Figure 37:
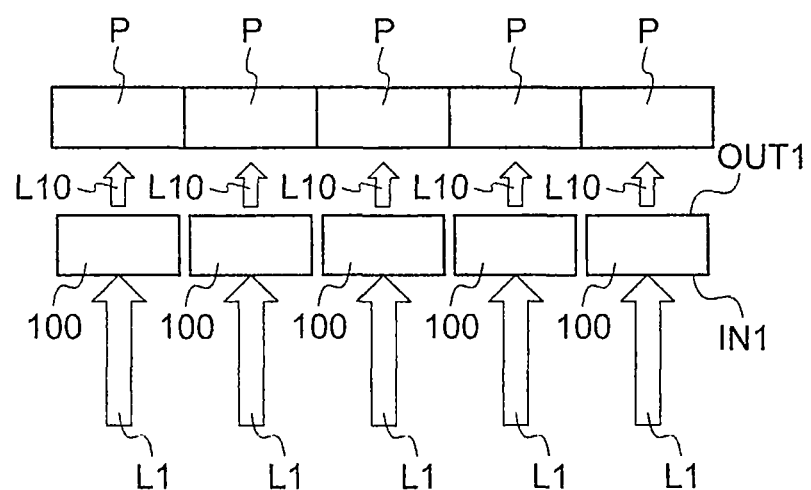
FIG. 37 is a diagram for describing a path of light entering an object in the light detection device.

FIG. 37 is a diagram for describing a path of light irradiating an object in the light detection device.

In this light detection device, a plurality of metamaterial optical members 100 are opposite to a plurality of objects P and arranged in a line. In the present example, each object P is a photodiode or a multiplier phototube. In this case, according to an intensity of light L1 incident on each metamaterial optical member 100, the collected light L10 emits from the metamaterial optical member 100 and incident on the line sensor. Signals of one-dimensionally distributed optical images are output from the line sensor.

Figure 38:
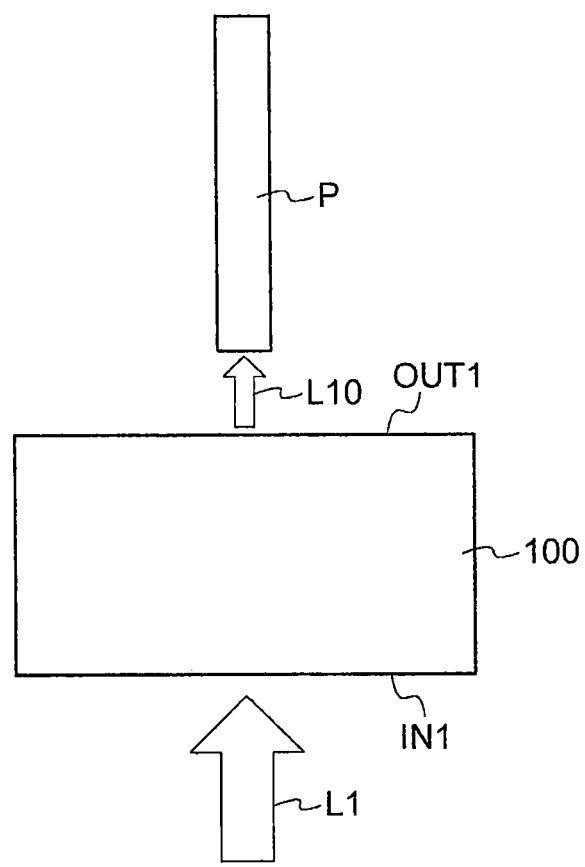
FIG. 38 is a diagram for describing a path of light entering an object in a laser excitation light source.

FIG. 38 is a diagram for describing a path of light irradiating an object in a laser excitation light source.

In the present example, a configuration in which light is not incident from the side of the object P, but is incident from one end of a longitudinal direction is provided. The incident light L1 is incident within the metamaterial optical member 100 via the light-entering surface IN1, internally collected, exits from the light-exiting surface OUT1 as the output light L10, and incident on an end surface of the object P. The object P is the laser medium and may be an optical waveguide such as an optical fiber. Here, it is possible to cause laser light for excitation light to be incident in multiple directions for the light-entering surface IN1 to concentrate light on the optical fiber. The metamaterial optical member 100 can generally cause incident light from a plurality of directions to be collected at the same position and can function as a plurality of excitation light couplers for one optical fiber.

Also, although an example in which light is incident on a light-entering surface of the metamaterial optical member at an angle of inciden1111111ce of 45 degrees has been described in the above-described embodiment, the angle of incidence of the light is not limited thereto. Light can be incident from various directing methods.

Figure 39:
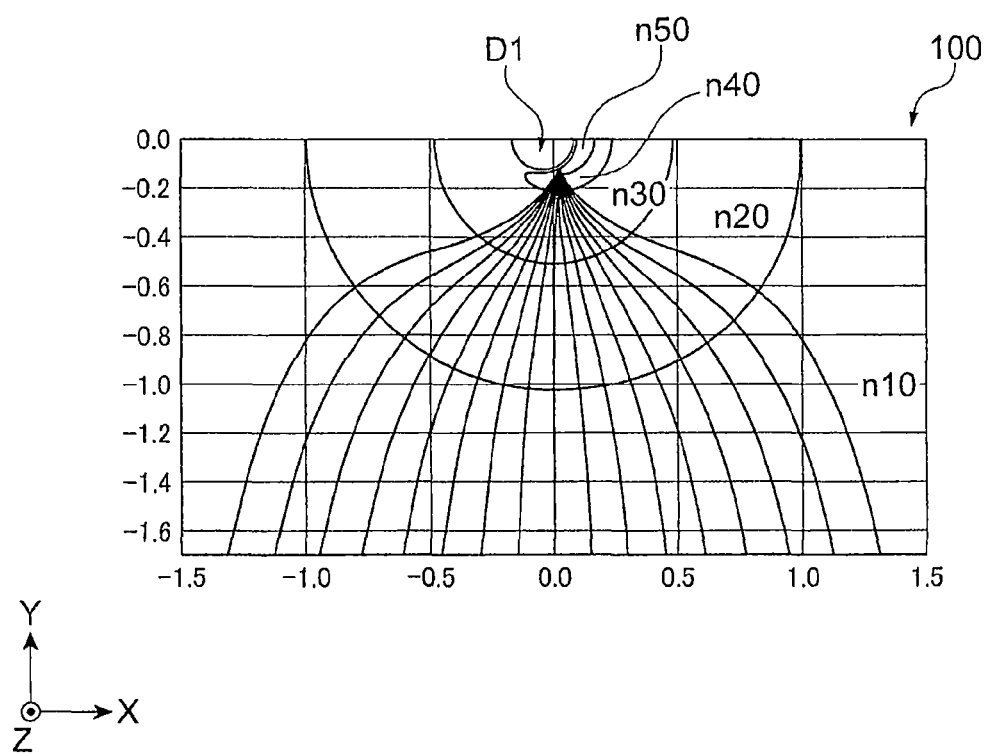
FIG. 39 is a diagram illustrating a path of light traveling within the metamaterial optical member of the input side.

FIG. 39 is a diagram illustrating a path of light traveling within the metamaterial optical member of the input side and illustrates a graph overlapping a position of the metamaterial optical member. Also, dimensions are indicated on a vertical axis and a horizontal axis and units of the dimensions are, for example, millimeters.

A state in which incident light is incident on the light-entering surface at 0 degrees is shown. Light entiring the light-entering surface is collected toward the concave portion D1. Because an antireflection film (not illustrated) is provided at a light collection position, the collected light is externally output without being reflected by an interface.

Figure 40:
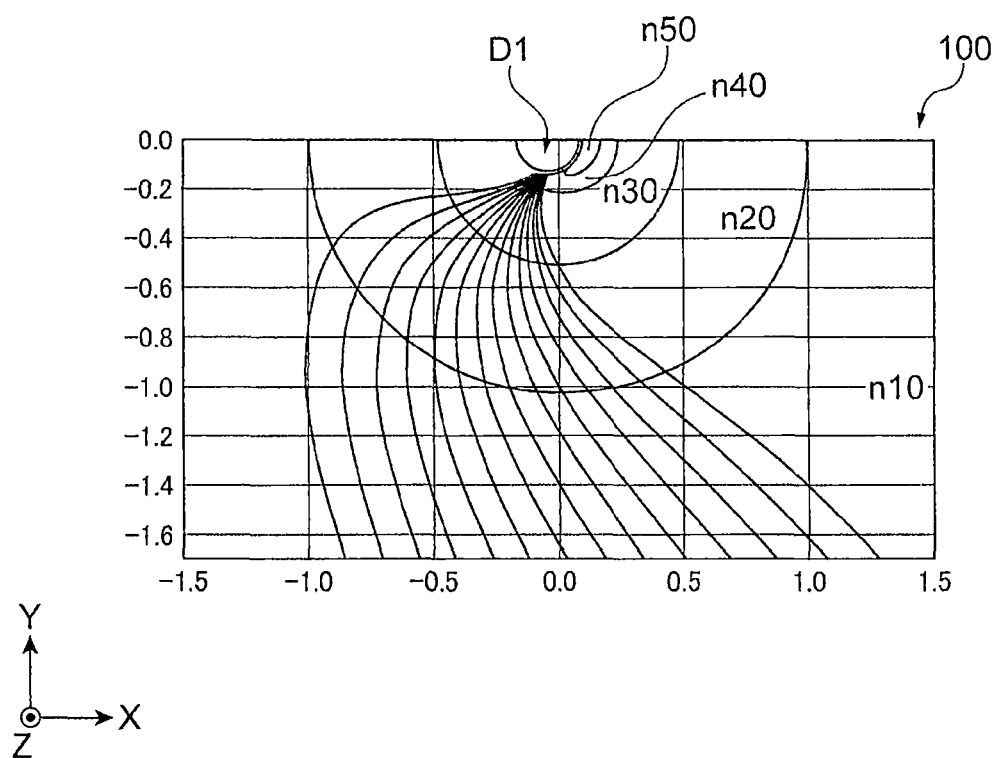
FIG. 40 is a diagram illustrating a path of light traveling within the metamaterial optical member of the input side.

FIG. 40 is a diagram illustrating a path of light traveling within the metamaterial optical member of the input side and illustrates a graph overlapping a position of the metamaterial optical member. Also, dimensions are indicated on a vertical axis and a horizontal axis and units of the dimensions are, for example, millimeters.

A state in which incident light is incident on the light-entering surface at 45 degrees in a direction opposite to the case of FIG. 14 is shown. The light entering the light-entering surface is collected toward the concave portion D1. After the incident light travels left in the drawing, the light is collected while being bent to the right and collected in an inner surface of the concave portion D1 through the region n40. Because an antireflection film (not illustrated) is provided at the light collection position, the collected light is externally output without being reflected by the interface.

Also, although the case in which the refractive index of the inside of the metamaterial optical member results from a refractive index distribution of Hook in FIGS. 14, 39, and 40 was described above, the refractive index may be in another distribution.

Figure 41:
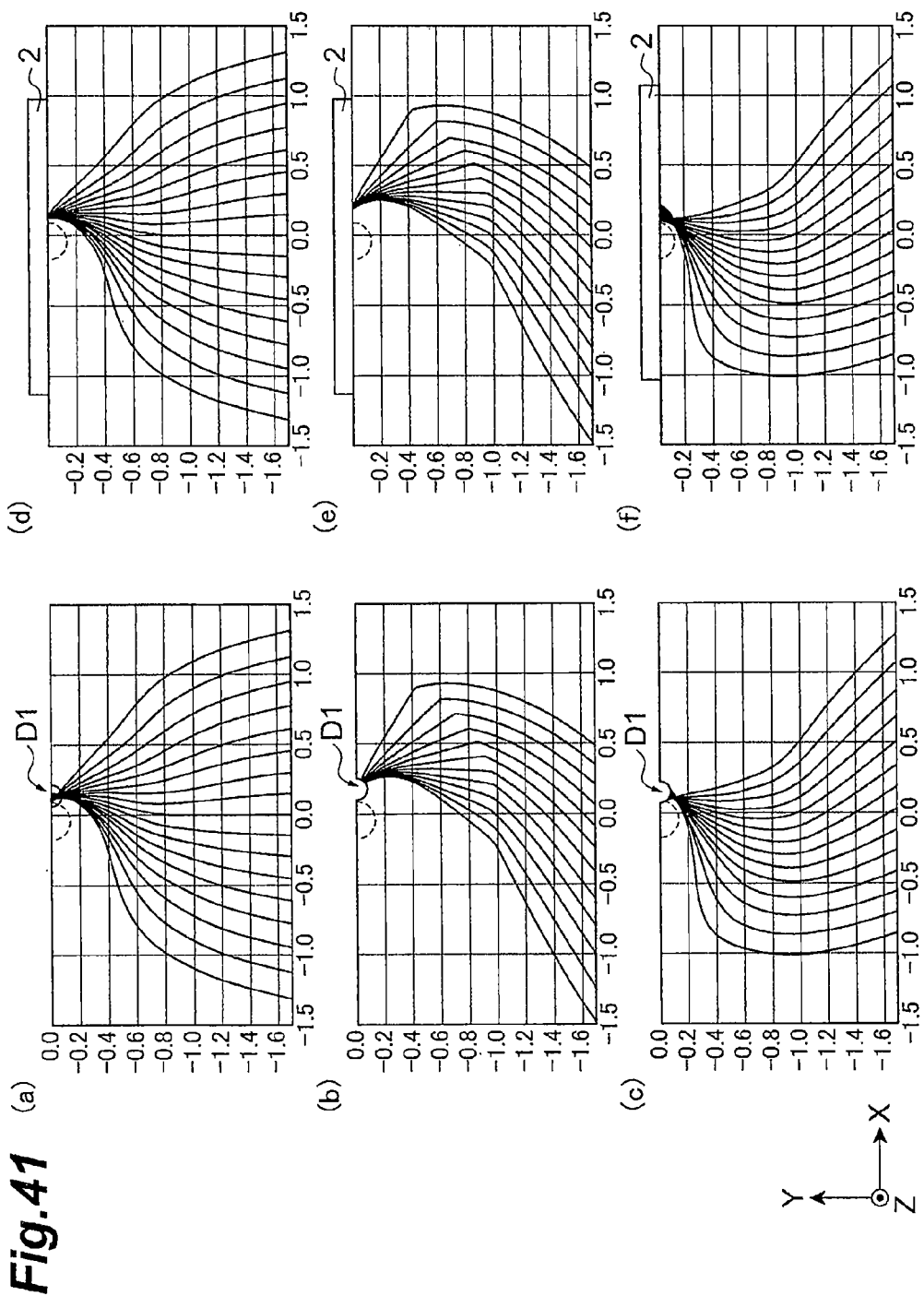
FIG. 41 is a diagram illustrating a path of light traveling within the metamaterial optical member of the input side.

FIG. 41 is a diagram illustrating a path of light in the case in which the refractive index distribution of the metamaterial optical member results from a refractive index distribution of Kepler, and illustrates a graph overlapping a position of the metamaterial optical member. FIG. 41(*a*) illustrates the case in which the angle of incidence is 0 degrees, FIG. 41(*b*) illustrates the case in which the angle of incidence is 45 degrees, and FIG. 41(*c*) illustrates the case in which the angle of incidence is −45 degrees. In the case of incidence from any direction, the incident light is collected toward the concave portion D1 of FIG. 41. The concave portion D1 of FIG. 41 is located at a position adjacent to the concave portion in place of the concave portion D1 (a position indicated by a dotted line) illustrated in FIG. 13 or the like described above and has a smaller radius than the concave portion. An inner surface of the concave portion D1 is a light-exiting surface and the antireflection film 2 (not illustrated) is disposed in a front surface of an inner surface (a concave surface of a semi-cylindrical shape). Incident light passing through the antireflection film 2 externally exits from the inner surface of the concave portion. An opening angle of an arc constituting the inner surface of the concave portion D1 within the XY-plane is 180 degrees, but another angle may be given.

FIG. 41(*d*) illustrates the case in which the angle of incidence is 0 degrees, FIG. 41(*e*) illustrates the case in which the angle of incidence is 45 degrees, and FIG. 41(*e*) illustrates the case in which the angle of incidence is −45 degrees, wherein the above-described concave portion is not provided, the light-exiting surface is a flat surface, and the antireflection film 2 is formed on the flat surface. Light exiting from the flat surface externally exits via the antireflection film 2. The structure of the antireflection film 2 is the same as that illustrated in FIG. 30.

Next, a method of designing a beam path in a metamaterial optical member will be described. In the above-described metamaterial optical member, incident light is collected in a specific region regardless of a direction of the incident light. A cloaking device (invisibility cloak) is known as a device for enabling light to be incident on a specific region. In the present invention, the antireflection film is arranged adjacent to the cloaking region in the cloaking device and extracts light (electromagnetic waves) from the outside (the outside of the cloaking region). An example in which the antireflection film is arranged in the concave portion by providing the concave portion in the vicinity of the cloaking region in one example and the antireflection film is arranged so that the vicinity of the cloaking region becomes the flat surface in another example has been described.

Therefore, a beam path for light collection in the metamaterial optical member can adopt a part of a beam distribution of the cloaking device (invisibility cloak). When the beam path of the invisibility cloak in the metamaterial optical member is designed, it is only necessary to design a refractive index distribution so that a beam is guided along the beam path. Also, for example, "New. J. Phys, vol. 8, 118 (2006)" is known as a method of calculating the beam path when there is a refractive index gradient.

In the design of the beam path, an optical conformal mapping method and a coordinate conversion method are known (for example, "Science, vol. 312, 1777 (2006)" and "Science, vol. 312, 1780 (2006)"). The conformal mapping method is a method of obtaining a beam trajectory by solving an approximate wave equation in a Helmholtz equation in a complex plane. This is a method of coupling two spaces through conformal mapping by designating a real space as a physical space (z-plane) and designating a temporary space to be used to facilitate the design as a virtual space (w-plane). As a method of the conformal mapping, for example, a Zhukovski transform can be used. A Zhukovski transform is used when the design is performed in the virtual space in order to easily perform the design in the physical space. A Zhukovski transform is conformal mapping for transforming the physical space (z-plane) into the virtual space (w-plane). The design using the optical conformal mapping method is useful when the metamaterial optical member is designed using an isotropic medium and the design of the metamaterial optical member using an anisotropic medium is useful when the coordinate conversion method is used.

Figure 42:
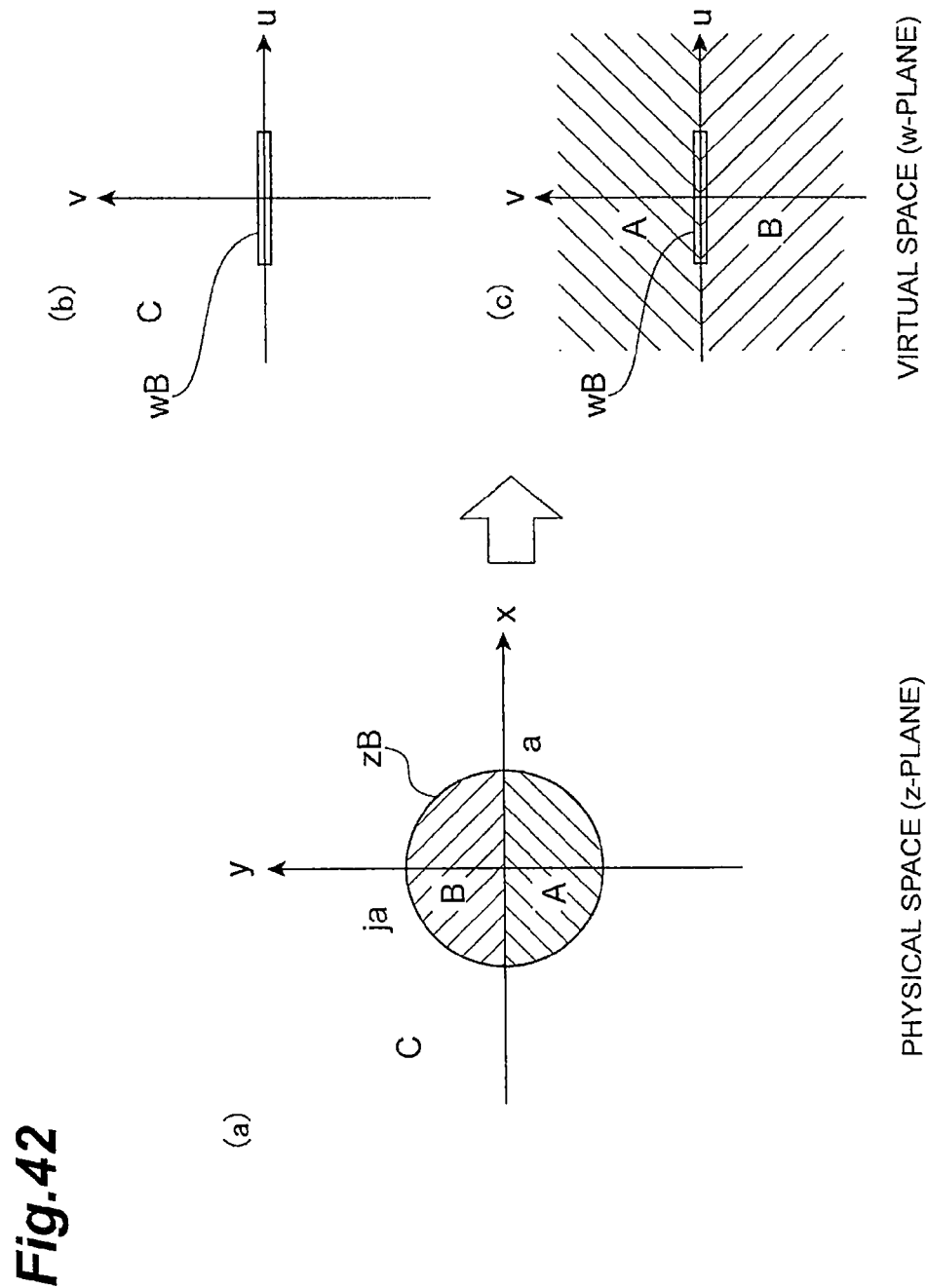
FIG. 42 is a diagram for describing a Zhukovski transform.

FIG. 42 is a diagram for describing a Zhukovski transform.

FIG. 42(*a*) illustrates a physical space (z-plane: z=x+jy) and FIGS. 42(*b*) and 42(*c*) illustrate a virtual space (w-plane: w=w=u+jv) (j is an imaginary unit) after the Zhukovski transform is performed on the physical space. Because these planes are complex planes, a real axis is set in the horizontal axis and an imaginary axis is set in the vertical axis.

A circle zB having a radius a is drawn in the z-plane in FIG. 42(*a*), but the circle zB is transformed into a line segment wB of FIG. 42(*b*) or FIG. 42(*c*) according to the Zhukovski transform (w=z+a²/z). Also, the line segment we of FIG. 42(*b*) or 42(*c*) is substantially transformed into the circle zB according to an inverse transform $(z=(w\pm(w^2-4a^2)^{1/2})/2$.

A region C outside the circle zB having the radius a in FIG. 42(*a*) becomes a region C for embedding the circumference of the line segment wB in FIG. 42(*b*) after the transform (FIG. 42(*b*)). An upper region B inside the circle zB having the radius a in FIG. 42(*a*) becomes a lower region B of the line segment zB in FIG. 42(*c*) after the transform. A lower region A inside the circle zB having the radius a in FIG. 42(*a*) becomes an upper region A of the line segment zB in FIG. 42(*c*) after the transform.

Because the number of points on the z-plane corresponding to one point on the w-plane is two, the function of the virtual space is a multi-valued function and this can be represented as a Riemann plane by superimposing the w-planes (FIG. 42(*b*) and FIG. 42(*c*)) of the virtual spaces sharing the line segment wB.

Also, because the origin position in FIG. 42(*a*) illustrating the physical space diverges to infinity in the virtual space after the transform, a beam does not pass through the origin in an actual physical space in a state in which light travels in a confined space in the virtual space.

Also, a refractive index distribution of Hook (a refractive index distribution by a harmonic oscillation profile method of Hook) and a refractive index distribution of Kepler (a refractive index distribution by a profile method of Kepler) are shown in a virtual space in the above-described example, but the Hook refractive index distribution is a refractive index distribution according to the following formula. A region having a radius $r_0$ can correspond to a circle z1 which is the above-described hollow region.

$$n'^2 = 1 - |w - w_1|/r_0$$

Here, n' denotes a refractive index in a Riemann sheet of a lower side of the virtual space, $r_0$ denotes a value of a radius to be used when a cloaking region is defined, w denotes one point on the Riemann sheet of the lower side of the virtual space, and $w_1$ denotes a value of a branch point in the virtual space.

Also, the Kepler refractive index is a refractive index distribution according to the following formula.

$$n'^2 = r_0/|w - w_1| - 1$$

Here, n' denotes a refractive index in a Riemann sheet of a lower side of the virtual space, $r_0$ denotes a value of a radius to be used when a cloaking region is defined, w denotes one point on the Riemann sheet of the lower side of the virtual space, and $w_1$ denotes a value of a branch point in the virtual space.

Figure 43:
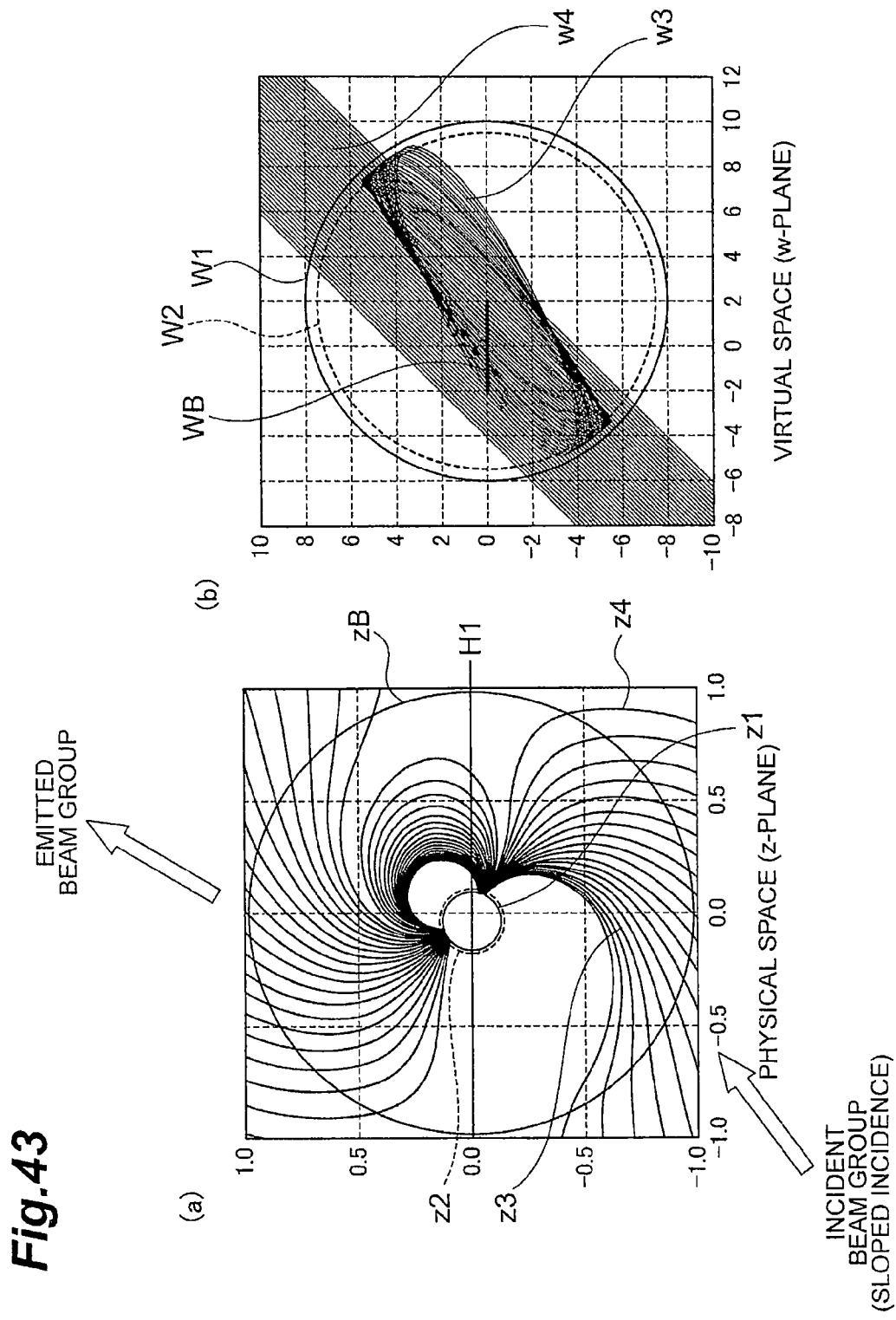
FIG. 43 is a diagram for describing beam groups (refractive index distributions of Hook) before and after the transform.

FIG. 43 is a diagram for describing beam groups (refractive index distributions of Hook) before and after the transform.

Figure 44:
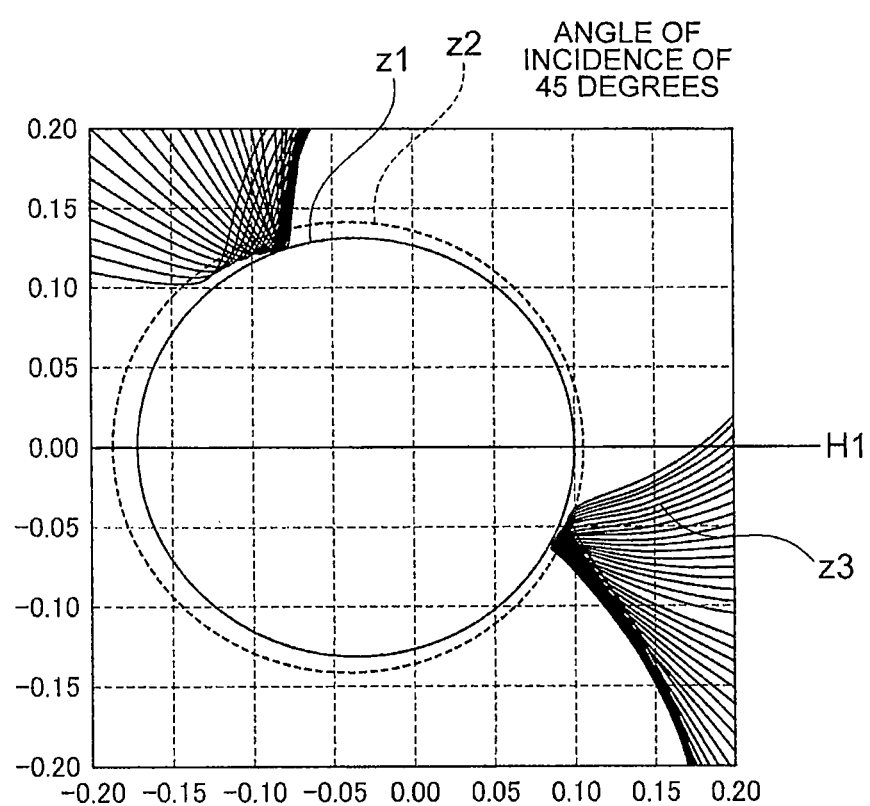
FIG. 44 is a diagram for describing a beam group in the vicinity of an invisibility cloak.

FIG. 43(*a*) is a diagram illustrating a beam locus group of a cloaking device in the physical space and a beam group necessary for designing the present invention, and scales are indicated on the vertical axis and the horizontal axis. The unit of the vertical axis and the unit of the horizontal axis are, for example, millimeters. When light is incident on a metamaterial optical member at an angle of incidence of 45 degrees from a lower side of the drawing, light is not incident inside the circle z1 in the vicinity of the origin when the metamaterial optical member is a cloaking device and light is bent in the vicinity of the circle z1 and externally output as an output beam. A circle z2 is drawn by a dotted line at a side slightly outward from the circle z1 and the incident light is externally exposed in the vicinity of a light collection position before being bent in the vicinity of the circle z1 when a process of removing an upper portion by cutting the metamaterial optical member along a horizontal line H1 passing through the center of the circle z1 and further performing removal up to a position of the circle z2 is performed. An enlarged view of a beam path in the vicinity of the circle z2 is illustrated in FIG. 44. It is possible to externally extract collected light by providing an antireflection film at this light collection position. Also, in FIG. 43(*a*), the above-described circle zB having the radius a is illustrated.

FIG. 43(*b*) is a diagram illustrating a beam path in the virtual space and scales are indicated on the vertical axis and the horizontal axis. The unit of the vertical axis and the unit of the horizontal axis are, for example, millimeters. A circle zB of FIG. 43(*a*) is transformed into a line segment wB of FIG. 43(*b*) according to a Zhukovski transform. Circles z1 and z2 located inside the circle zB are transformed into circles w1 and w2 in a virtual space, respectively. A beam path z4 outside the circle zB in the physical space and a beam path z3 inside the circle zB are transformed into a parallel beam group w4 and an annular beam group w3 in the virtual space, respectively.

Figure 45:
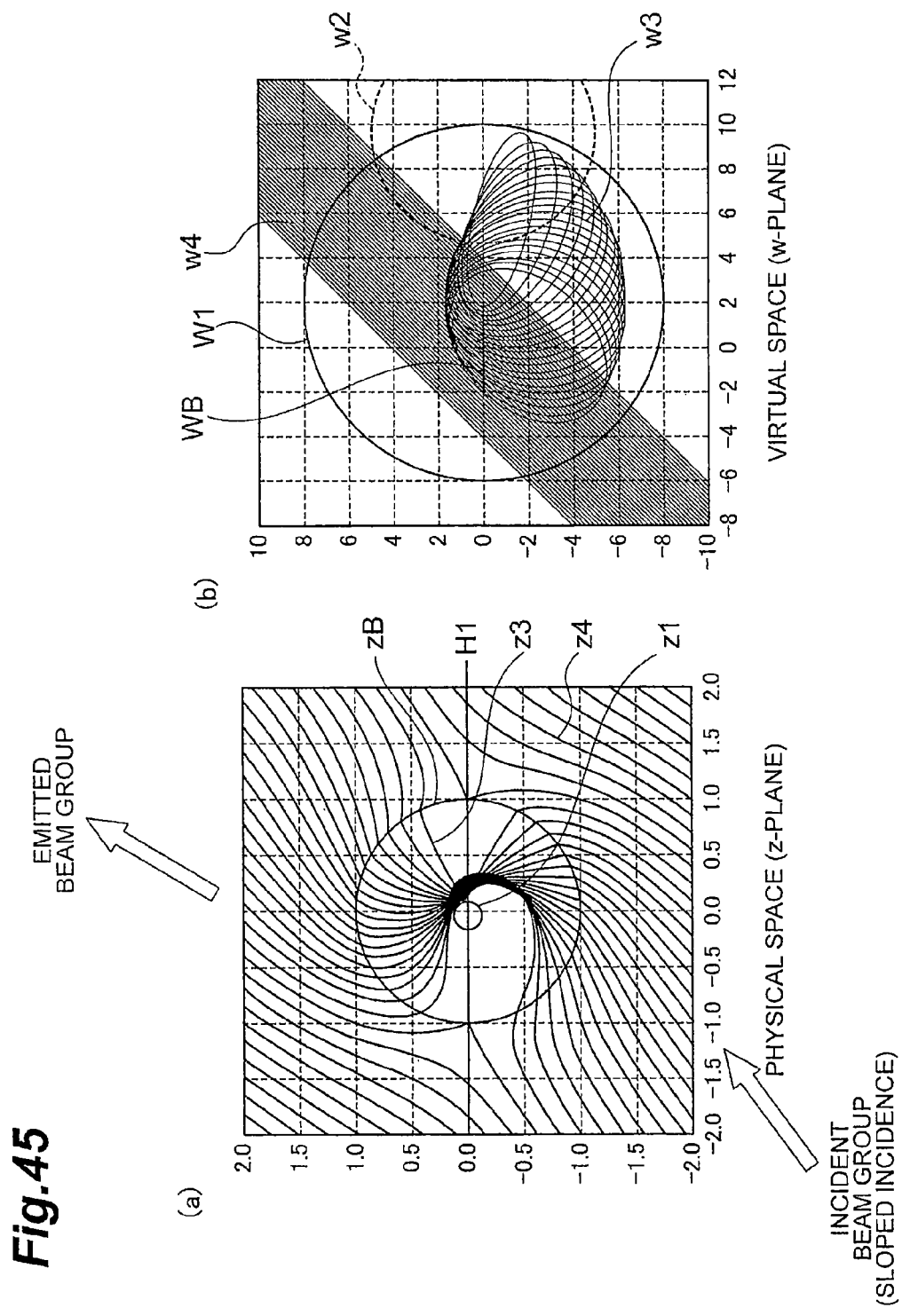
FIG. 45 is a diagram for describing beam groups (refractive index distributions of Kepler) before and after the transform.

FIG. 45 is a diagram for describing beam groups (refractive index distributions of Kepler) before and after the transform.

Figure 46:
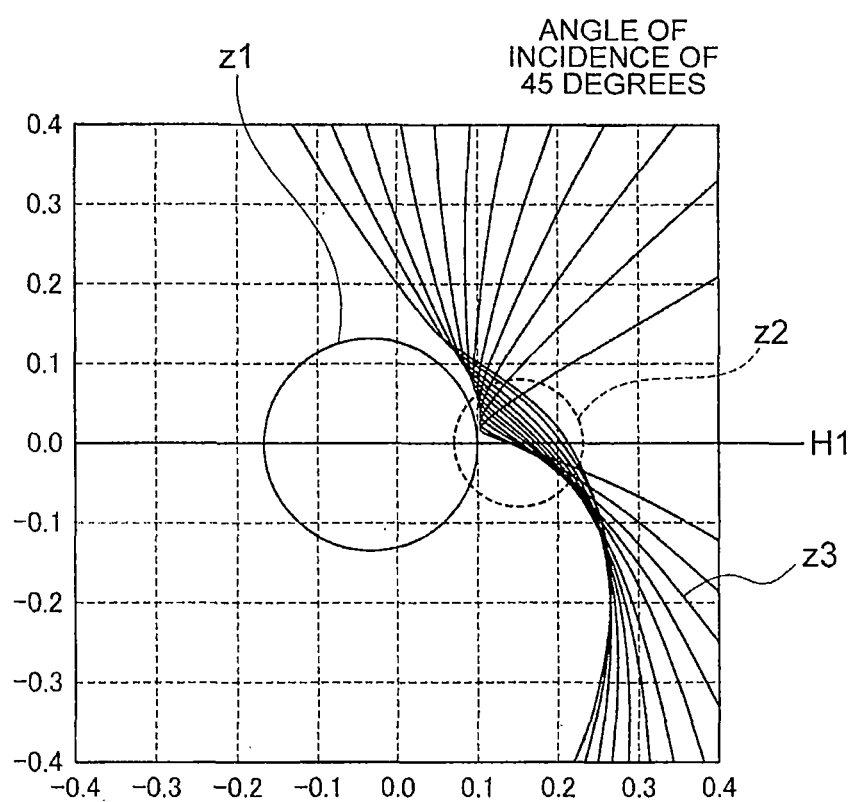
FIG. 46 is a diagram for describing a beam group in the vicinity of an invisibility cloak.

FIG. 45(*a*) is a diagram illustrating a beam path in the physical space and scales are indicated on the vertical axis and the horizontal axis. The unit of the vertical axis and the unit of the horizontal axis are, for example, millimeters. When light is incident on a metamaterial optical member at an angle of incidence of 45 degrees from a lower side of the drawing, light is not incident inside the circle z1 in the vicinity of the origin when the metamaterial optical member is a cloaking device and light is bent in the vicinity of the circle z1 and externally output as an output beam. Incident light is collected in the vicinity of a specific position on a horizontal line H1 across the circle z1. When a process of cutting the metamaterial optical member along the horizontal line H1 passing through the center of the circle z1 and removing the upper portion is performed, incident light is externally exposed in the vicinity of a light collection position before the incident light is bent in the vicinity of the circle z1. An enlarged view of a beam path in the vicinity of the circle z1 is illustrated in FIG. 46. It is possible to externally extract collected light by providing an antireflection film at this light collection position. Also, as illustrated in FIG. 46, it is possible to perform a process of removing a region of a circle z2 surrounding the vicinity of the light collection position and provide an antireflection film at a position of removal. Also in FIG. 45(*a*), the above-described circle zB having the radius a is illustrated.

FIG. 45(*b*) is a diagram illustrating a beam path in the virtual space and scales are indicated on the vertical axis and the horizontal axis. The unit of the vertical axis and the unit of the horizontal axis are, for example, millimeters. A circle zB is transformed into a line segment wB of FIG. 45(*b*) according to a Zhukovski transform. A circle z1 and a circle z2 (illustrated in FIG. 46 but not in FIG. 45(*a*)) located inside the circle zB are transformed into circles w1 and w2 in a virtual space, respectively. A beam path z4 outside the circle zB in the physical space and a beam path z3 inside the circle zB are transformed into a parallel beam group w4 and an annular beam group w3 in the virtual space, respectively.

Also, the above-described beam path indicates the case in which the angle of incidence is 45 degrees, but FIG. 47 illustrates a line path in the vicinity of the circle z1 when the angle of incidence is 30 degrees (FIG. 47(*a*)) and the angle of incidence is 0 degrees (FIG. 47(*b*)) (refractive index distribution of Kepler). Because a beam z3 is reflected according to the circle z1 as described above, it is possible to externally extract the collected light by performing a process of cutting an upper region by a horizontal line passing through a circle or further removing a region indicated by a circle z2 and providing an antireflection film in the vicinity of an exposed light collection position.

Based on the above principle, in the present embodiment, a beam path in the metamaterial optical member is designed using a Zhukovski transform between the physical space and the virtual space and an inverse transform. That is, a cloaking region is corrected according to sequential computation to obtain a necessary part from a beam locus group of a cloaking device using an optical conformal mapping method.

As described above, a metamaterial optical member according to the above-described embodiment and a device using the metamaterial optical member have the above-described configuration and characteristics.

A first metamaterial optical member 100 according to the above-described embodiment includes a light collecting optical member 1 having a light-entering surface IN1 and a light-exiting surface OUT1 and having a light collecting function; and an antireflection film 2 disposed in the light-exiting surface OUT1 of the light collecting optical member 1, wherein the antireflection film 2 has a first metamaterial structure in which a refractive index is gradually reduced in the light travelling direction (see FIGS. 6 and 7). A refractive index of a region in which light is collected by the light collecting optical member 1 is set to be higher than that of its peripheral region. Accordingly, the antireflection film 2 of the first metamaterial structure is provided so that light collected in the light-exiting surface OUT1 of the light collecting optical member 1 is externally extracted without being reflected by the light-exiting surface OUT1. Because it is possible to form a refractive index change from a high refractive index absent in the natural world to a low refractive index using the metamaterial structure, it is possible to externally extract light which is not externally extracted conventionally.

Also, in a second metamaterial optical member 100 of the above-described embodiment, the light collecting optical member 1 has a second metamaterial structure in which a refractive index gradually increases from the light-entering surface IN1 to the light-exiting surface OUT1 (see FIG. 13). In this case, because the light collecting optical member 1 can have the second metamaterial structure and form the refractive index change absent in the natural world, it is possible to perform light collection using a shape or a diameter which could not be implemented in the past. It is possible to externally extract light collected in the light-exiting surface OUT1 even when light collection of such a special state is performed because the antireflection film 2 of the first metamaterial structure is provided.

In a third metamaterial optical member 100 according to the above-described embodiment, the light-exiting surface Mill includes a concave surface (concave portion D1) (FIG. 1). In this case, a light collection position of the light collecting optical member 1 is set to be positioned inside the concave surface, so that the collected light can be used within an inside space of the concave portion D1.

In a fourth metamaterial optical member 100 according to the above-described embodiment, the light-exiting surface OUT1 includes a second concave surface (concave portion D2) continuous to a part of the concave surface and having a smaller opening size than the concave surface (FIG. 18). When the light collection position is positioned at a deeper position in the light collecting optical member than the concave surface of the concave portion D1, the second concave surface inside which the light collection position is positioned is partially provided. The second concave surface can be formed even when a large portion of the light collecting optical member 1 is not processed because the opening size is small.

In a fifth metamaterial optical member 100 according to the above-described embodiment, the light-exiting surface OUT1 includes a flat surface (FIG. 30). In this case, there is an advantage in that it is unnecessary to perform a process of forming a concave surface in the light-exiting surface OUT1.

A first light detection device using a metamaterial optical member according to the above-described embodiment includes the third or fourth metamaterial optical member 100 having the above-described concave surface; and a light detector arranged inside a concave surface of the metamaterial optical member. When light to be detected is incident on the light-entering surface IN1 of the light collecting optical member 1, the light to be detected is collected and incident on the light detector arranged inside the concave surface via the antireflection film 2. Therefore, the light detector can detect light to be detected. A multiplier phototube, a photodiode, a solid-state imaging element, or the like can be used as the light detector.

Also, a first laser excitation light source according to the above-described embodiment includes the third or fourth metamaterial optical member 100 having the above-described concave surface; and a laser medium arranged inside a concave surface of the metamaterial optical member 100. When excitation light of the laser medium is incident on the light-entering surface IN1 of the light collecting optical member 1, the light is collected and incident on the light detector arranged inside the concave surface via the antireflection film 2. Therefore, the excitation light can excite the laser medium. It is possible to use an optical fiber or the like to which a rare earth element such as Er, Yb, or Nd is added as the laser medium.

A first measuring device according to the above-described embodiment includes the third or fourth metamaterial optical member 100 having the above-described concave surface; a medium flow path arranged inside a concave surface of the metamaterial optical member 100; and a light detector configured to detect light from the medium flow path (FIG. 1). Materials of various inspection targets can flow within the medium flow path. For example, in the case in which a labeling material for generating fluorescence flows when light of a specific wavelength is absorbed inside the medium flow path, the light detector can detect light generated from the material and the analysis of the material, etc. can be performed on the basis of the detected light. Also, when an opaque liquid flows as a medium, it is possible to inspect the transparency of the medium by detecting an intensity of light transmitted through the medium.

A second light detection device according to the above-described embodiment includes the fifth metamaterial optical member 100 having the above-described flat surface; and a light detector arranged opposite to the flat surface of the metamaterial optical member 100. When light to be detected is incident on the light-entering surface IN1 of the light collecting optical member 1, the light to be detected is collected and incident on the light detector via the antireflection film 2 disposed in the flat surface. Therefore, the light detector can detect light to be detected. A multiplier phototube, a photodiode, a solid-state imaging element, or the like can be used as the light detector. In particular, when the flatness of the flat surface is used, there is an advantage in that solid-state imaging elements are easily arranged opposite to each other.

A second laser excitation light source according to the above-described embodiment includes the fifth metamaterial optical member 100 having the above-described flat surface; and a laser medium arranged opposite to a flat surface of the metamaterial optical member 100. When excitation light of the laser medium is incident on the light-entering surface of the light collecting optical member, the light is collected and incident on the laser medium arranged opposite to the antireflection film via the antireflection film 2 disposed in the flat surface. Therefore, the excitation light can excite the laser medium. An element having a plate shape in which an opposite surface is flat as well as an optical fiber or the like to which a rare earth element such as Er, Yb, or Nd is added can be used as the laser medium.

A second measuring device according to the above-described embodiment includes the fifth metamaterial optical member 100; a medium flow path arranged opposite to a flat surface of the metamaterial optical member 100; and a light detector configured to detect light from the medium flow path. The materials of the inspection targets described above can flow within the medium flow path. The light detector can detect light generated from the material inside the medium flow path and the analysis of the material, etc. can be performed on the basis of the detected light. Also, when an opaque liquid flows as a medium, it is possible to inspect the transparency of the medium by detecting an intensity of light transmitted through the medium.

Also, when light emission from the laser medium, the medium flow path, or the like is detected, a second metamaterial optical member 200 to be used in combination with the first metamaterial optical member 100 can be used (FIG. 1). The second metamaterial optical member 200 of a side at which light is received as described above includes a light transfer member 1A having a light-entering surface IN2 and a light-exiting surface OUT2; and an antireflection film 2A disposed in the light-entering surface IN2 of the light transfer member 1A, wherein the light transfer member 1A has a refractive index which is gradually reduced from the light-entering surface IN2 to the light-exiting surface OUT2. Because the region of the light-entering surface IN2 has a high refractive index, light can easily be incident from the outside. When the light is incident from the outside to the light-entering surface IN2 of the light transfer member 1A, the antireflection film 2A functions and the transfer loss of light is suppressed. Because the metamaterial structure can form the refractive index absent in the natural world, the second metamaterial optical member 200 can transfer light symmetric to the first metamaterial optical member 100 and therefore a design is simplified by performing a common design of a refractive index distribution or the like.

As described above, in the case of a metamaterial optical member 200 of a light-receiving type, the light-entering surface IN2 includes a concave surface and receives light from a medium flow path or a laser medium arranged within the concave surface. The light transfer member 1A transfers the incident light, so that the transferred light can be output from the light-exiting surface. Also, the metamaterial optical member 200 can transfer light from the object P arranged within the concave portion to the light-exiting surface OUT2, but the metamaterial optical member 100 can collect light entering inside via the light-entering surface IN1 in various directions toward the inside of the concave portion.

REFERENCE SIGNS LIST

100 First metamaterial optical member
1 Light collecting optical member
2 Antireflection film
1A Light transfer member
2A Antireflection film
P Object
200 Second metamaterial optical member

The invention claimed is:
1. A light detection device comprising:
  a metamaterial optical member comprising;
    a light collecting optical member having
      a light-entering surface and
      a light-exiting surface and
      wherein the light collecting optical member is configured to collect light that enters the light-entering surface; and
    an antireflection film disposed in the light-exiting surface of the light collecting optical member,
      wherein the antireflection film comprises a first metamaterial structure in which a refractive index is gradually reduced in the light travelling direction,
      wherein the light-exiting surface includes a concave surface; and
  a light detector disposed inside a concave surface of the metamaterial optical member.
2. The metamaterial optical member according to claim 1, wherein the light-exiting surface includes a second concave surface continuous to a part of the concave surface and having a smaller opening size than the concave surface.
3. The metamaterial optical member according to claim 1, wherein the light collecting optical member comprises a second metamaterial structure in which a refractive index gradually increases from the light-entering surface to the light-exiting surface.
4. A laser excitation light source comprising:
  a metamaterial optical member comprising:
    a light collecting optical member having
      a light-entering surface and
      a light-exiting surface and
      wherein the light collecting optical member is configured to collect light that enters the light-entering surface; and
    an antireflection film disposed in the light-exiting surface of the light collecting optical member,
      wherein the antireflection film comprises a first metamaterial structure in which a refractive index is gradually reduced in the light travelling direction,
      wherein the light-exiting surface includes a concave surface; and
  a laser medium disposed inside a concave surface of the metamaterial optical member.
5. The metamaterial optical member according to claim 4, wherein the light-exiting surface includes a second concave surface continuous to a part of the concave surface and having a smaller opening size than the concave surface.
6. The metamaterial optical member according to claim 4, wherein the light collecting optical member comprises a second metamaterial structure in which a refractive index gradually increases from the light-entering surface to the light-exiting surface.
7. A measuring device comprising:
  a metamaterial optical member comprising;
    a light collecting optical member having
      a light-entering surface and
      a light-exiting surface and
      wherein the light collecting optical member is configured to collect light that enters the light-entering surface; and an antireflection film disposed in the light-exiting surface of the light collecting optical member,
wherein the antireflection film comprises a first metamaterial structure in which a refractive index is gradually reduced in the light travelling direction,
wherein the light-exiting surface includes a concave surface;
a medium flow path disposed inside a concave surface of the metamaterial optical member; and
a light detector configured to detect light from the medium flow path.

8. The metamaterial optical member according to claim 7, wherein the light-exiting surface includes a second concave surface continuous to a part of the concave surface and having a smaller opening size than the concave surface.

9. The metamaterial optical member according to claim 7, wherein the light collecting optical member comprises a second metamaterial structure in which a refractive index gradually increases from the light-entering surface to the light-exiting surface.

* * * * *